(12) United States Patent
Murata

(10) Patent No.: US 7,914,663 B2
(45) Date of Patent: Mar. 29, 2011

(54) STRUCTURE, POROUS BODY, SENSOR, PROCESS OF STRUCTURE AND DETECTING METHOD FOR SPECIMEN

(75) Inventor: Yusuke Murata, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 1039 days.

(21) Appl. No.: 10/590,293

(22) PCT Filed: Jun. 1, 2006

(86) PCT No.: PCT/JP2006/311469
§ 371 (c)(1),
(2), (4) Date: Aug. 23, 2006

(87) PCT Pub. No.: WO2006/132294
PCT Pub. Date: Dec. 14, 2006

(65) Prior Publication Data
US 2009/0014338 A1    Jan. 15, 2009

(30) Foreign Application Priority Data
Jun. 7, 2005   (JP) ................................. 2005-166754

(51) Int. Cl.
*G01N 27/327* (2006.01)
*C12Q 1/68* (2006.01)
*G01N 33/543* (2006.01)
*C12Q 1/26* (2006.01)
*B01D 24/00* (2006.01)

(52) U.S. Cl. ..................... 205/778; 204/403.01; 422/50; 436/518; 435/25; 435/26; 210/500.1

(58) Field of Classification Search ............ 204/403.01–403.15; 205/777.5, 778, 792; 210/500.1, 210/500.21, 500.27; 436/518; 435/25, 26; 422/50

See application file for complete search history.

(56) References Cited

U.S. PATENT DOCUMENTS

| | | | | |
|---|---|---|---|---|
| 4,945,125 A * | 7/1990 | Dillon et al. | ................... | 524/427 |
| 5,624,875 A | 4/1997 | Nakanishi et al. | ............... | 501/39 |
| 5,964,993 A * | 10/1999 | Blubaugh et al. | ........ | 204/403.09 |
| 6,696,258 B1 | 2/2004 | Wei et al. | ........................ | 435/7.2 |
| 6,699,382 B2 * | 3/2004 | Yoshioka et al. | ........... | 205/777.5 |
| 6,733,828 B2 * | 5/2004 | Chao et al. | ..................... | 427/239 |
| 6,958,480 B1 * | 10/2005 | Iyer et al. | ...................... | 250/340 |
| 7,001,669 B2 * | 2/2006 | Lu et al. | ........................ | 428/613 |
| 2004/0122121 A1 | 6/2004 | Loureiro et al. | .............. | 521/153 |
| 2005/0063890 A1 | 3/2005 | Nakanishi | ..................... | 423/335 |

FOREIGN PATENT DOCUMENTS

JP         06-265534         9/1994

(Continued)

OTHER PUBLICATIONS

Online Merriam-Webster dictionary definition of "dendritic", which was downloaded on Oct. 25, 2010.*

(Continued)

*Primary Examiner* — Alex Noguerola
(74) *Attorney, Agent, or Firm* — Fitzpatrick, Cella, Harper & Scinto

(57) ABSTRACT

A mesoporous silica structure having a plurality of mesopores includes a dendritic framework having mesopores. 90% or more of the mesopores observable in a 500 nm×500 nm area pass through the framework in a direction perpendicular to a longitudinal direction of the framework.

9 Claims, 16 Drawing Sheets

FOREIGN PATENT DOCUMENTS

| | | |
|---|---|---|
| JP | 2002-080216 | 3/2002 |
| WO | WO 03/002458 | 1/2003 |

OTHER PUBLICATIONS

S. Shio, et al., "Morphological Control of Ordered Mesoporous Silica: Formation of Fine and Rod-Like Mesoporous Powders from Completely Dissolved Aqueous Solutions of Sodium Metasilicate and Cationic Surfactants", XP-002397874, Chem. Commun., pp. 2461-2462 (1998).

H. Zhang, et al., "Unusual Mesoporous SBA-15 with Parallel Channels Running Along the Short Axis", XP-002397875, Journal of the American Chemical Society, vol. 126, No. 24, pp. 7440-7441 (2004).

D. Zhao, et al., "Triblock Copolymer Syntheses of Mesoporous Silica with Periodic 50 to 300 Angstrom Pores", XP-002397876, Science Coden, vol. 279, No. 23, pp. 548-552 (Jan. 23, 1998).

* cited by examiner

STRUCTURE, POROUS BODY, SENSOR, PROCESS OF STRUCTURE AND DETECTING METHOD FOR SPECIMEN

This application is a 371 of PCT/JP2006/311469, filed Jun. 1, 2006, and claims foreign priority from Japanese application 2005-166754, field Jun. 7, 2005.

TECHNICAL FIELD

The present invention relates to a new structure having a plurality of mesopores, a porous material, a sensor, and a method for producing the structure, and a method for detecting a specimen.

BACKGROUND ART

As porous materials, zeolites and silica gel have hitherto been known. Zeolites made of aluminosilicates have been practically applied as adsorbents and ion exchange materials, and further, as catalysts. Zeolites are crystalline, have uniform pore sizes, and have excellent properties; however, the pore sizes thereof are as small as about 1 nm or less, and hence zeolites cannot be used as adsorbents or the like for organic compounds larger than the pore sizes. Silica gel has a larger pore size than zeolites; however, the pore size distribution extends widely, which raises a problem of controlling the structure of silica gel.

With such background, there have been developed materials referred to as mesoporous materials in which pores larger than those of zeolites and uniform in pore size are regularly arranged. Mesoporous materials are produced by taking advantage of surfactants, and there have been reported mesoporous materials that are formed of oxides such as $SiO_2$, $TiO_2$ and $ZrO_2$.

As external shapes of mesoporous materials, the following shapes have been reported: an external shape that has no branched portions and is particulate as shown in FIG. 15 (J. Am. Chem. Soc., 126, 2004, 7440-7441 (Non-patent Document 1)), and an external shape that has a branched structure (hereinafter, referred to as "dendritic") as shown in FIG. 16 (Chem. Commu., 1998, 2461-2462 (Non-patent Document 2)).

Hereinafter, when a mesoporous material is referred to, the whole solid portion of the mesoporous material such as a particulate mesoporous material shown in FIG. 15 and a dendritic mesoporous material shown in FIG. 16 will be particularly referred to as the "framework" of the mesoporous material. The pore shapes of the mesoporous materials have been known to be tubes passing through the framework or to be spheres confined within the framework.

As described above, active studies have been developed on mesoporous materials, but as main structures of mesoporous materials, there have been known only those described in Non-patent documents 1 and 2. Thus, mesoporous materials having new structure that are to be used for functional devices such as biosensors have been strongly demanded.

DISCLOSURE OF THE INVENTION

The present inventors have diligently studied the structure control for the purpose of obtaining a structure having mesopores, and consequently have perfected the present invention by discovering that a new structure can be produced.

A mesopore means a pore having a pore size of 2 nm or more and 50 nm or less, as defined by IUPAC (International Union of Pure and Applied Chemistry). According to IUPAC, a pore having a pore size less than 2 nm is defined as a micropore, and a pore having a pore size larger than 50 nm is defined as a macropore.

An object of the present invention is to provide a new structure having mesopores.

Another object of the present invention is to provide a porous material, a sensor and a method for detecting a specimen that take advantage of the new structure. According to an aspect of the present invention, there is provided a structure having a plurality of mesopores, comprising:

a dendritic framework having mesopores passing through the framework in the direction intersecting the longitudinal direction of the framework.

The mesopores are preferably perpendicular to the longitudinal direction of the framework.

The dendritic framework preferably forms macropores by mutual linking of branched portions of the framework, or macropore-sized voids are preferably formed between the frameworks adjacent to one another.

The mesopores are hexagonally symmetrically arranged, preferably.

The mesopores preferably have a pore size distribution in which 80% or more of the mesopores fall within a range having a width of 10 nm and a maximal value.

A biological material is preferably supported in the mesopores.

According to another aspect of the present invention, there is provided a porous material formed of a plurality of particles, comprising the particle comprised of the above structure.

According to still another aspect of the present invention, there is provided a sensor for detecting a specimen, which sensor is comprised of the above porous material and an electrode, and detects an electric output signal based on a reaction between the specimen and a biological material supported in the mesopores.

According to a further aspect of the present invention, there is provided a method for detecting a specimen, comprising the steps of:

preparing a sensor in which a biological material is supported in the mesopores of the above structure;

applying a fluid that contains a specimen to the sensor; and detecting an output signal based on a reaction between the biological material and the specimen.

According to the present invention, there can be provided a structure capable of being applied as a new functional material. For example, there can be provided a porous material suitable for columns and the like. Further, when used as a sensor, there can be provided a sensor higher in sensitivity than conventional sensors.

BEST MODE FOR CARRYING OUT THE INVENTION

Figure 1A:
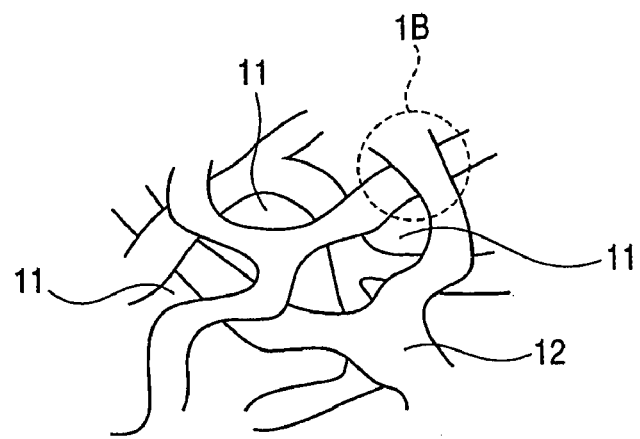
FIGS. 1A, 1B and 1C are schematic views of the structures according to the present invention.

A structure having mesopores according to the present invention is dendritic. Being dendritic is a concept that includes not only a shape in which the structure of a framework simply has branched structure, namely, a branched shape, but a shape in which a framework is continuously branched. The present invention also include as one embodiment thereof a dendritic framework that forms a three dimensional network structure as shown in the SEM micrograph of FIG. 2A and the SEM micrograph of FIG. 2B as taken with a higher magnification than in FIG. 2A, and a schematic view of FIG. 1A. The embodiment that adopts a three-dimensional network structure will be described below with reference to FIGS. 1A, 1B, 1C, 2A and 2B.

(Framework Structure)

Figure 3:
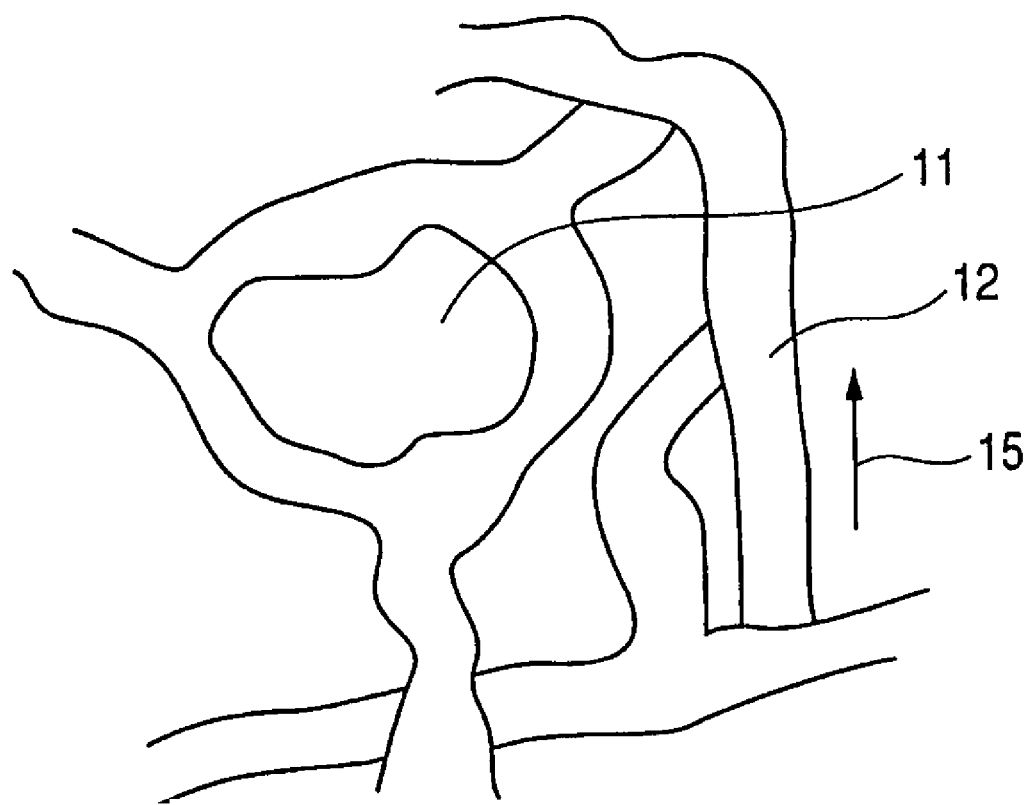
FIG. 3 is a schematic view illustrating a form of a macropore.

A void 11 in a dendritic framework 12 the portions of which are adjacent to each other to form a three dimensional network structure is preferably a macropore, namely, a void that ensures a pore having a projected area in a certain direction equal to or larger than the area of a circle having a diameter of 50 nm or more; in other words, the size of the void 11 is preferably larger than 50 nm, more preferably 100 nm or more and 700 nm or less. In particular, the spaces in the framework in such a case as shown in FIG. 3 wherein the branched framework undergoes linkage to form macropores is preferably such that the pore sizes of the macropores are 50 nm or more, and more preferably 100 nm or more and 700 nm or less.

Figure 1B:
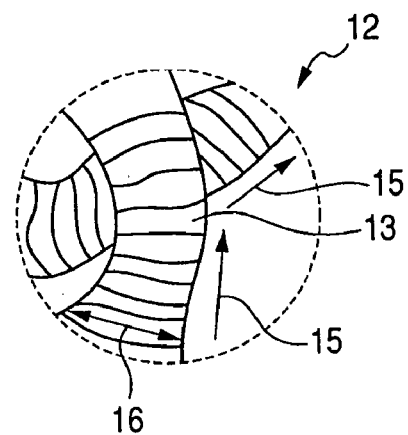
Figure 1C:
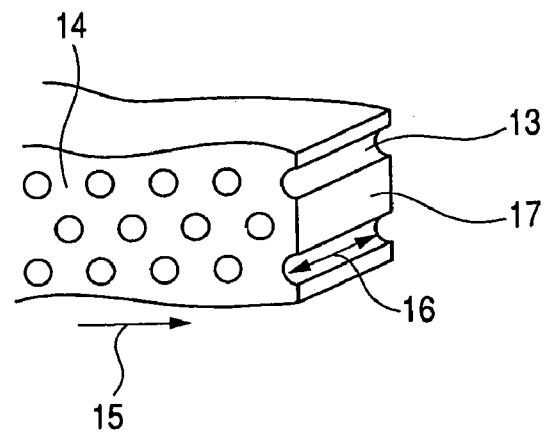

FIG. 1B is an enlarged view showing a portion of the framework 12, and FIG. 1C is an enlarged view showing the surface 14 of the framework 12 and the section 17 along the above described direction 16. As shown in FIGS. 1B and 1C, the mesopores 13 pass through the framework 12 in the direction 16 intersecting the longitudinal direction 15. The mesopores 13 have the openings thereof on the surface 14. The framework itself constituting the portion between the mesopores forms the "wall" separating the mesopores from each other.

Figure 2A:
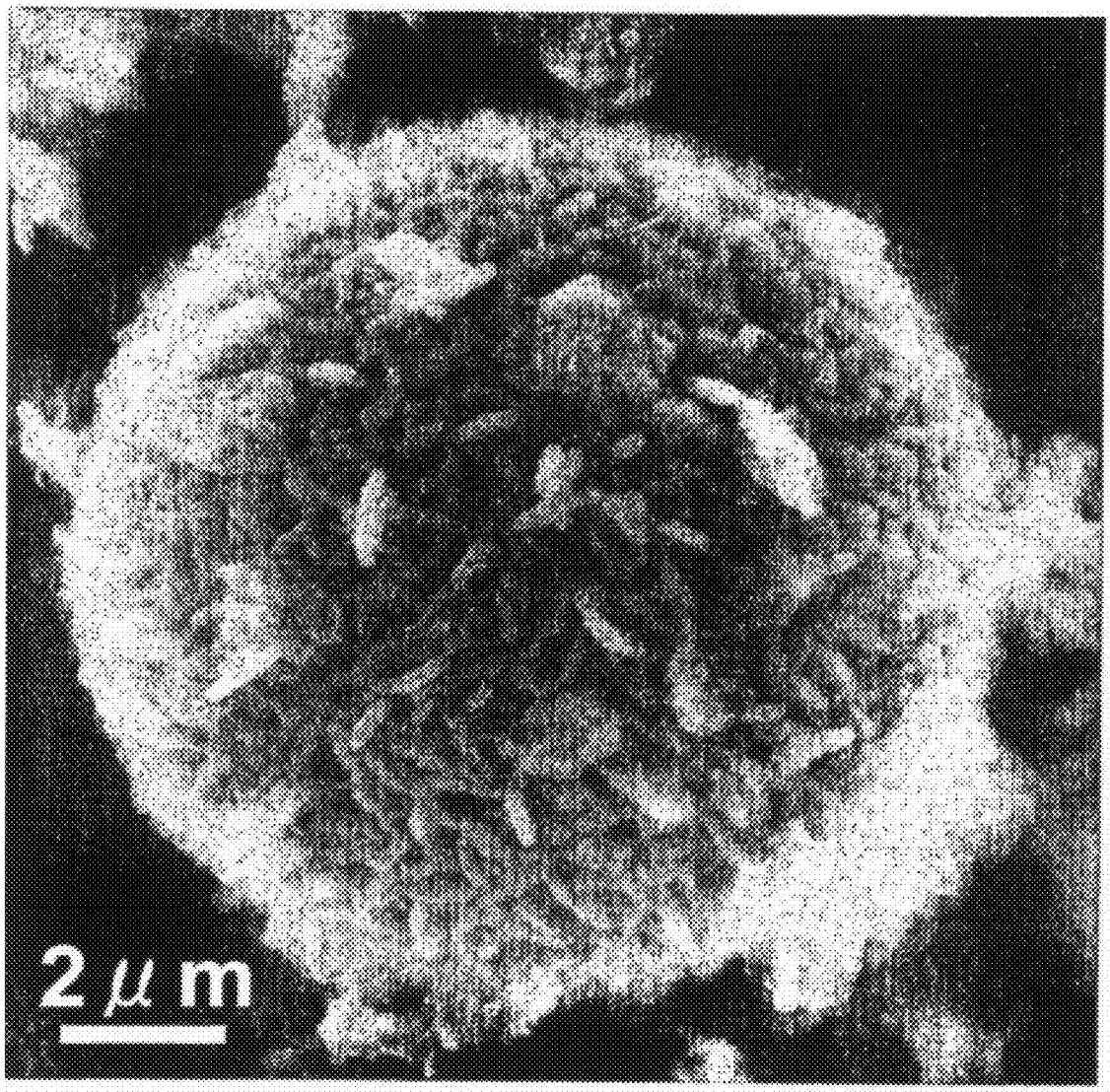
FIGS. 2A and 2B are the photos of the structures according to the present invention as observed with a scanning electron microscope.

The structure of the present invention may take macroscopically a shape of particle or film, but a shape of particle as shown in FIG. 2A is preferably used.

(Shapes, Pore Sizes, Configurations and Lengths of Mesopores)

The pore size of a mesopores is a diameter if the sectional shape of the mesopore is a circle, and is the length of the longest axis if the sectional shape of the mesopore is a deformed circle such as an ellipse. A powdery structure having mesopores is subjected to a measurement of nitrogen gas adsorption, and from the results of the measurement, the pore size distribution is derived on the basis of the Berret-Joyner-Halenda (BJH) method.

The pore size distribution of a structure to be preferably used in the present invention exhibits a single maximum value and 60% or more of the mesopores in the pore size distribution concerned fall within a range having a width of 10 nm and including the maximum value. According to an example to be described later, for example, the pore sizes of 80% or more of the fine pores fall within a range of ±5 nm from the maximum value, namely, in a range of having a width of 10 nm and including the maximum value. More preferably, 90% or more of the fine pores fall within a range having a width of 10 nm.

The pore sizes of the mesopores used in the present invention are 2 nm or more and 50 nm or less, more preferably 10 nm or more and 30 nm or less. Depending on the type of the application of the structure according to the present invention, for example, when the structure according to the present invention is applied to a biosensor, the pore sizes are preferably 10 nm or more so that a biological material such as an antibody may be introduced into the mesopores, and are preferably 30 nm or less from the viewpoint of the stabilization of the conformation of the biological material.

The shape of a mesopore may be such that the pore size thereof is monotonically increased or discontinuously varied from one opening thereof to the other opening thereof.

Figure 4A:
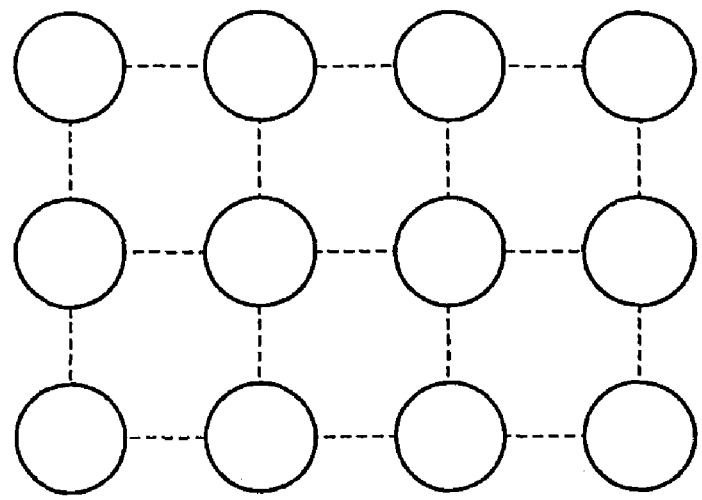
FIGS. 4A and 4B are schematic views illustrating a configuration of mesopores.
Figure 4B:
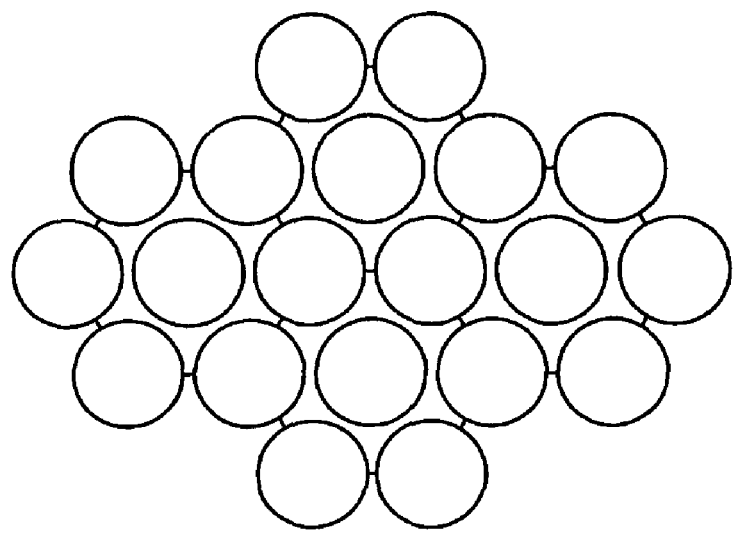

Information for the periodicity of the mesopores can be obtained from X-ray diffraction (XRD) measurement. The configuration of the mesopores as viewed in the direction normal to a section is not limited to a matrix configuration as shown in FIG. 4A, or a hexagonally symmetric configuration as shown in FIG. 4B, but may be another regular or irregular configuration. The structure according to the present embodiment has at least one diffraction peak in an angular region corresponding to a structure periodicity of 1 nm or more in XRD measurement; this means that the mesopores are regularly arranged.

The mutual separations between the mesopores are of the order of 1 nm to 4 nm. It is more preferable that a plurality of adjacent mesopores share the same direction of extension; however, the direction of these mesopores may be branched somewhere along the mesopores into a plurality of directions.

The length of a mesopore is preferably 50 nm or more and 500 nm or less. From the viewpoint of taking advantage of the mesopores as a reaction field for a biosensor or the like, the length of a mesopore is more preferably 50 nm or more and 300 nm or less.

The mesopores 13 are aligned evenly along the longitudinal direction 15 of the framework 12 as shown in FIG. 1B. The mesopores 13 are preferably aligned as perpendicularly as possible to the longitudinal direction 15 of the framework 12. In an area, for example, a 500 nm×500 nm area, observable with an electron microscope, 90% or more of the mesopores are preferably aligned along the perpendicular direction.

(Constituent Materials)

As a material constituting the framework 12, namely, the pore wall of the mesopores, oxides such as silicon oxide, titanium oxide or tin oxide are preferable. Such a material may be a hybrid material composed of an inorganic material such as silica and an organic material such as benzene or ethylene.

A coating layer made of a silane coupling agent or the like can be formed on the pore inner wall of the mesopores, or an enzyme, an antibody, DNA or the like can be introduced into the mesopores to be supported therein. For example, the pore surface (pore inner wall) can be modified with a silane coupling agent, or with an aqueous solution of a metal salt that contains a metal capable of forming an oxide.

(Method for Producing the Structure)

For the purpose of producing the structure having mesopores according to one embodiment of the present invention, a reaction solution that contains a material to form the framework of the structure, a surfactant and an orientation controlling agent is heated to 120° C. in the presence of a hydrolysis catalyst, so that a structure containing the surfactant is formed under the hydrothermal synthesis conditions, and then the surfactant is removed from the structure. Specific description will be made below.

First, the prepared reaction solution is added with the hydrolysis catalyst, stirred at around room temperature, and thereafter, the raw materials are allowed to undergo condensation polymerization reaction in a range from a few hours to a few days.

Then, the precipitate produced in the solution is collected, washed and then dried. Then, the surfactant is removed from the precipitate. In this way, there is obtained a structure that has mesopores passing through the framework along a direction intersecting the longitudinal direction of the framework.

The materials to be the raw materials for the framework include halogen compounds, chalcogen compounds or metal alkoxides. When the pore wall of mesopores is formed with silicon oxide, tetraethoxysilane and tetramethoxysilane that are metal alkoxides are preferably used.

As the surfactant, nonionic surfactants such as block copolymers that contain polyethylene oxide as hydrophilic groups are preferably used.

The orientation controlling agent may be an organic matter that can orient the surfactant so as to intersect the longitudinal direction of the dendritic framework; examples of such an organic matter may, include n-decane ($C_{10}H_{22}$). The detailed mechanism of the orientation controlling agent applied in the present invention is under study; when the orientation of the surfactant is along a direction intersecting the longitudinal direction of the framework, a sate stable in terms of entropy would be created. It is conceivable that by setting the reaction time at a few hours to a few days and the temperature at the time of reaction at 120° C., silicon oxide is laminated before it forms particles, or the silicon oxide particles undergoing reaction are mutually bonded, and thus dendritic growth is resulted. The temperature of 120° C. is the ambient atmosphere temperature of the furnace for heating the solution; the solution is placed in a pressure vessel and the temperature of the solution is substantially the same as the ambient atmosphere temperature.

The dendritic structure thus obtained can be collected with a centrifugal separator because it is precipitated in the solution. The collected precipitate is dried by air drying or the like.

A porous material can be obtained by removing the surfactant forming micelles from the collected precipitate. No particular constraint is imposed on the method for removing the surfactant as long as the method is a method capable of removing the surfactant without destroying the fine pore structure. Examples of such a method may include a method in which the surfactant is dissolved in a solvent so as to be removed, a method in which the surfactant is extruded from the pores by applying a supercritical state fluid, and further, a method in which the surfactant is oxidized to be removed by use of ozone. More preferable is a method in which the surfactant is removed by calcining the structure in an oxygen-containing atmosphere; in this method, the structure is calcined in air at 550° C. for 5 hours, and consequently the surfactant can be removed without substantially destroying the mesoporous structure. The calcining temperature and time are appropriately selected according to the material to form the fine pore wall or the framework and the surfactant to be used.

By additionally applying the following steps to the structure obtained on the basis of the above described method, a biological material support can be produced.

Specifically, the step means a method in which the structure having mesopores is soaked in a solution containing a biological material and the biological material is adsorbed in the pores of the porous material by stirring. For the purpose of facilitating the introduction of the biological material into the mesopores, a functional group (for example, an amino group or a carboxyl group) may be introduced onto the fine pore surface (pore wall surface) of the mesopores; in this way, a biological material is easily introduced into the mesopores conceivably because the functional group located on the pore wall surface and the biological material electrically interact with each other.

For example, there is a method in which the fine pore surface is modified with a silane coupling agent, and a method in which the fine pore surface is modified with an aqueous solution of a metal salt containing a metal capable of forming an oxide. The silane coupling agent is a compound generally represented by the chemical formula R—Si—$X_3$, and having two or more different functional groups in a molecule thereof. The X denotes a site capable of reacting with the surface of the porous material made of an inorganic material. For example, in Journal of Sol-Gel Science, 1989, 662, a case where a mesoporous material is silicon oxide is described; the hydrogen atoms of the silanol groups located on the fine pore surface are substituted with organic silicon groups to form the Si—O—Si—R bonds, and thus a layer of an organic matter R is formed on the fine pore surface; examples of X include a chloro group, an alkoxy group, an acetoxy group, an isopropenoxy group and an amino group. Needless to say, there can be used a silane coupling agent in which X is bifunctional or monofunctional as well as a silane coupling agent in which X is trifunctional as long as the silane coupling agent can react with the fine pore surface to form the layer of R. R stands for an organic group such as an amino group, a carbonic group or a maleimide group.

When the fine pore surface is modified with an aqueous solution of a metal salt-containing an element capable of forming an oxide, titanium, aluminum, zirconium, tin or the like can be used as an element capable of forming the oxide layer concerned. For example, by treating mesoporous silica with an aqueous solution of zirconium oxynitrate, a layer of zirconium oxide can be formed on the surface.

Figure 5A:
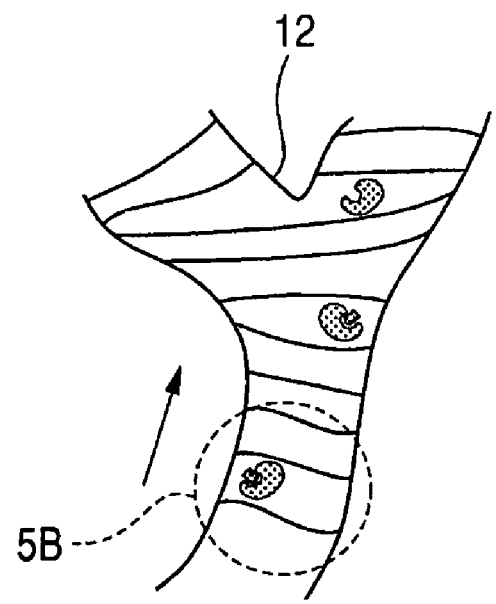
FIGS. 5A and 5B are schematic views illustrating a case where a structure according to the present invention is made to support a biological material.
Figure 5B:
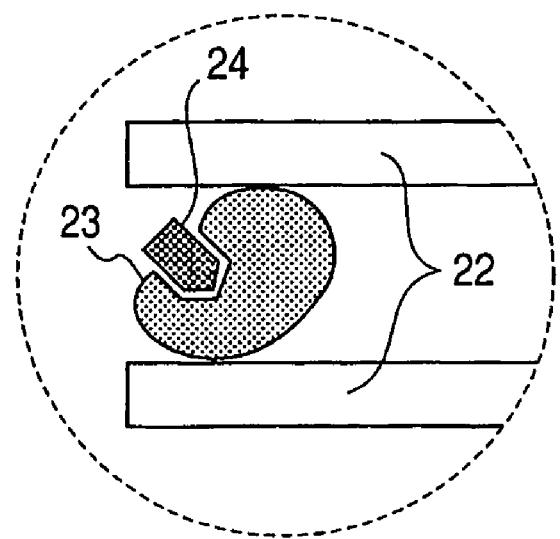

FIGS. 5A and 5B are schematic views illustrating a structure supporting a biological material in the mesopores.

FIGS. 5A and 5B show views of a state in which the biological material 23 is surrounded by the pore wall 22 of the mesopores to be supported. Reference numeral 12 denotes the framework shown in FIGS. 1A, 1B and 1C. When such a biological material support is used as a biosensor, there is applied a phenomenon in which the biological material 23 and a material 24 having a specific affinity with the biological material 23 react with each other, as shown in an enlarged manner in FIG. 5B.

The present inventors have been studying the structures suitable as the reaction fields for enzymatic reactions and antigen-antibody reactions, and have discovered that the structure according to the present invention is suitable as such reaction fields.

The biological materials to be used in the present invention are antibodies, antibody fragments, DNAs, proteins, enzymes and the like. The biological materials also include the fragments containing active sites of a single strand DNA and Fab antibodies and the like. The DNA fragments may also be those fragments which are extracted from animals, plants and microbes, and cut to desired shapes, or those which are genetically engineered or chemically synthesized.

Examples of the material 24 may include antigens, antibody fragments, DNAs, proteins and enzymes. For example, when the biological material 23 is an antibody, the material 24 having a specific affinity with the biological material is an antigen.

Although not shown, there is preferably provided an anchor to connect the inner surface of the pore wall 22 of the mesopores to the biological material 23.

This anchor has an effect to suppress the large structural change of the biological material and thus to stably maintain the structure of the biological material. The components to constitute an anchor are preferably the same constituent materials as the materials constituting the structure having mesopores. The anchor preferably has, as the site for bonding to the biological material, a hydroxy group, an amide group, an amino group, a pyridine group, a urea group, a urethane group, a carbonic group, a phenol group or the like. Further, the anchor may also be a compound that has a functional group such as an azo group, a hydroxyl group, a maleimide group, a silane derivative or an aminoalkylene group.

Each of the mesopores can accommodate one or more biological materials. Accordingly, the mesopores each are required to have a size appropriate to immobilize the biological material.

When the size of the mesopores and the size of the biological material to be immobilized in the mesopores fit to each other, the surface of the biological material is close to the pore wall of the mesopores, so that the biological material is adsorbed in the mesopores by the van der Waals force due to the pore wall of the mesopores. Accordingly, the conformation of the biological material is furthermore maintained, so that the deactivation of the biological material due to the conformational change can be furthermore suppressed. The active units can be held in the mesopores by noncovalent bonding such as electrostatic bonding, hydrogen bonding and ionic bonding as well as the van der Waals force.

(Functional Devices Using the Structure According to the Present Invention)

Next, functional devices using the structure according to the present invention will be described.

As described above, a structure supporting a biological material in the mesopores thereof can be applied to a biosensor as a functional device.

In other words, a method for detecting a specimen according to one embodiment of the present invention will be described.

First, there is prepared a sensor in which a biological material is supported in the mesopores of the above described structure, and the sensor is provided with a fluid (liquid or gas) containing the specimen. Then, the fluid containing the specimen penetrates into the mesopores while passing through the voids and macropores of the dendritic structure, and reacts with the biological material supported in the mesopores. The voids and macropores of the structure having the dendritic framework each have a large conductance to the fluid, so that the fluid evenly reaches the whole structure having the dendritic framework, and furthermore, reaches the mesopores communicatively connected to the voids and macropores. When the longitudinal direction of the mesopores and the longitudinal direction of the framework are parallel to each other, the openings of the mesopores on the side wall of the framework are very low in occurrence probability, so that the probability of the penetration of the specimen into the mesopores becomes very low. In the present invention, the longitudinal direction of the mesopores and the longitudinal direction of the framework intersect with each other, and consequently there is detected the output signal based on the reaction between the biological material and the specimen occurring in a large number of the mesopores of the structure, so that the sensitivity is improved.

For details, the detection principle of the specimen takes advantage of the antigen-antibody reaction between an antigen and an antibody, a specific bonding reaction such as a bonding reaction between a single DNA and another single DNA, or other reactions. In any case, a target material is detected by taking advantage of variations of physical quantities such as electric current, electric voltage, light quantity, mass and heat quantity. Examples of the detection devices may include an enzyme electrode, a hydrogen peroxide electrode, an ISFET (Ion Sensitive Field Effect Transistor), an optical fiber, a thermistor, a quarts oscillator and a surface plasmon resonator.

The structure according to the present invention can be used as a column of an adsorbent or a separating agent, as a functional device other than biosensors. In this case, a large number of particles made of the above described structure of the present embodiment are prepared, and the particles may be compacted to produce a porous material.

When an electrode is installed by combining the porous material with an electron transfer element, the above described variations of the physical quantities can be detected as electric output signals.

Hereinafter, the present invention will be described in detail with reference to examples.

EXAMPLES

Example 1

In this Example, description will be made on a structure in which the pore wall material of the mesopores is silica.

First, 2.40 g of a nonionic surfactant, namely, a triblock copolymer ($EO_{20}PO_{70}EO_{20}$; $HO(CH_2CH_2O)_{20}(CH_2CH(CH_3)O)_{70}(CH_2CH_2O)_{20}H$) was dissolved in 76.5 ml of purified water. Further, the aqueous solution obtained was added with 7.5 ml of 36% by weight of concentrated hydrochloric acid, and stirred at room temperature for 30 minutes. Then, the aqueous solution was added with 13.9 g of n-decane, as an orientation controlling agent, and was stirred at room temperature for 2 hours.

Further, this mixed solution was added with 0.027 g of NH$_4$F as a hydrolysis catalyst and 5.10 g of tetraethoxysilane (TEOS) to prepare a precursor solution. The final composition (in molar ratio) of the precursor solution was made to satisfy the following ratio: TEOS:HCl:EO$_{20}$PO$_{70}$EO$_{20}$: NH$_4$F:n-decane =25:90:0.4:0.7:100.

The precursor solution was stirred at 40° C. for 20 hours, and then allowed to react at 120° C. for 48 hours. The white precipitate thus obtained was washed with purified water sufficiently and dried under a vacuum.

The powder sample thus obtained was calcined at 550° C. in air, and thus the surfactant was decomposed and removed from the interior of the fine pores to form hollow fine pores. The removal of the organic matters such as the surfactant was checked by the infrared absorption spectrum measurement method.

Figure 6:
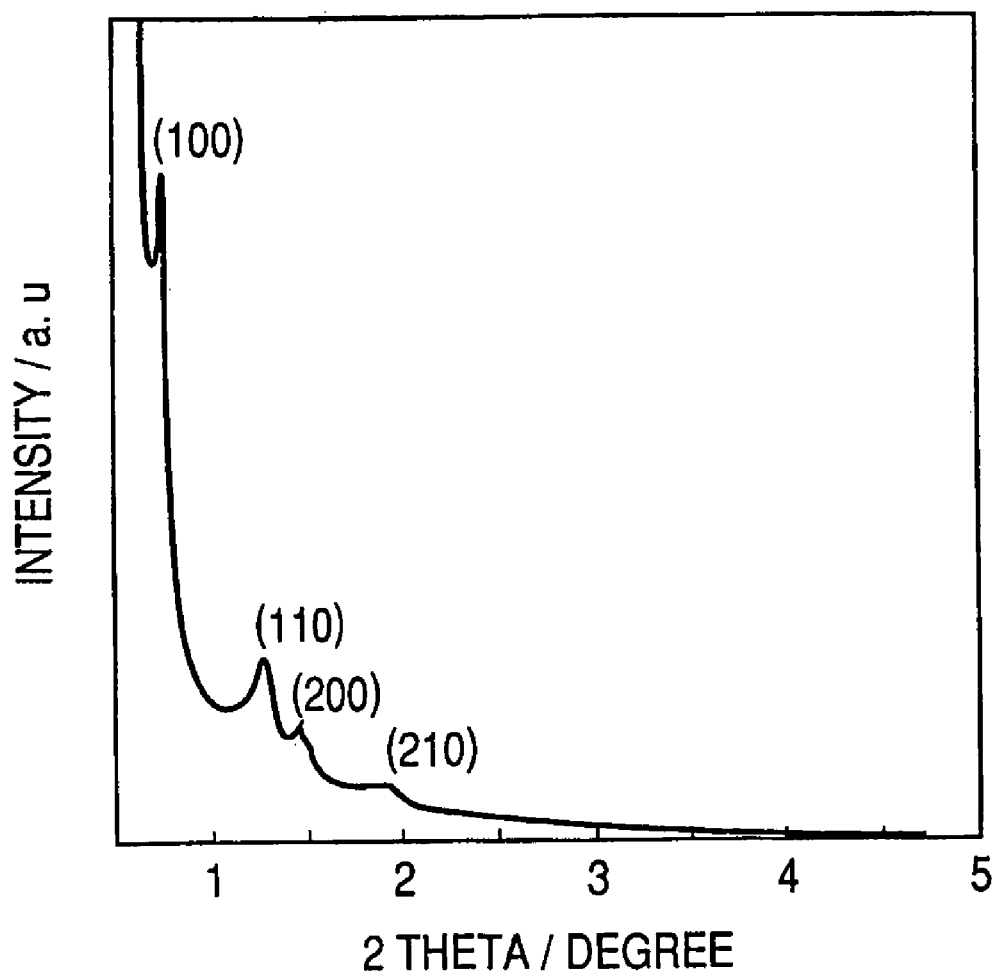
FIG. 6 is a graph showing the results of X-ray diffraction of a mesoporous silica produced in Example 1.

The mesoporous silica powder thus synthesized was evaluated by means of the X-ray diffraction method, and consequently, as shown in FIG. 6, there were identified a diffraction peak to be assigned to the (100) plane, and also diffraction peaks to be assigned to the (110), (200) and (210) planes of a hexagonal structure with an interplanar distance of 11.7 nm. These results manifest that the fine pore structure of the mesoporous silica has a hexagonal array provided with a high regularity.

A nitrogen adsorption-desorption isotherm measurement was carried out at 77 K, and consequently, the shape of the adsorption isotherm was identified to be of the IV type according to the IUPAC classification. The specific surface area and the fine pore volume derived on the basis of the B.E.T. method were 700 m$^2$/g and 1.88 ml/g, respectively. From the results of the adsorption isotherm, the fine pore size was derived on the basis of the BJH method. Thus, the fine pore size distribution of the mesoporous silica synthesized in present Example exhibited a narrow distribution with a single peak at 14.3 nm. There was obtained a structure having a pore size distribution such that 90% or more of the mesopores fell within a range of 10 nm including the maximum value.

Figure 2B:
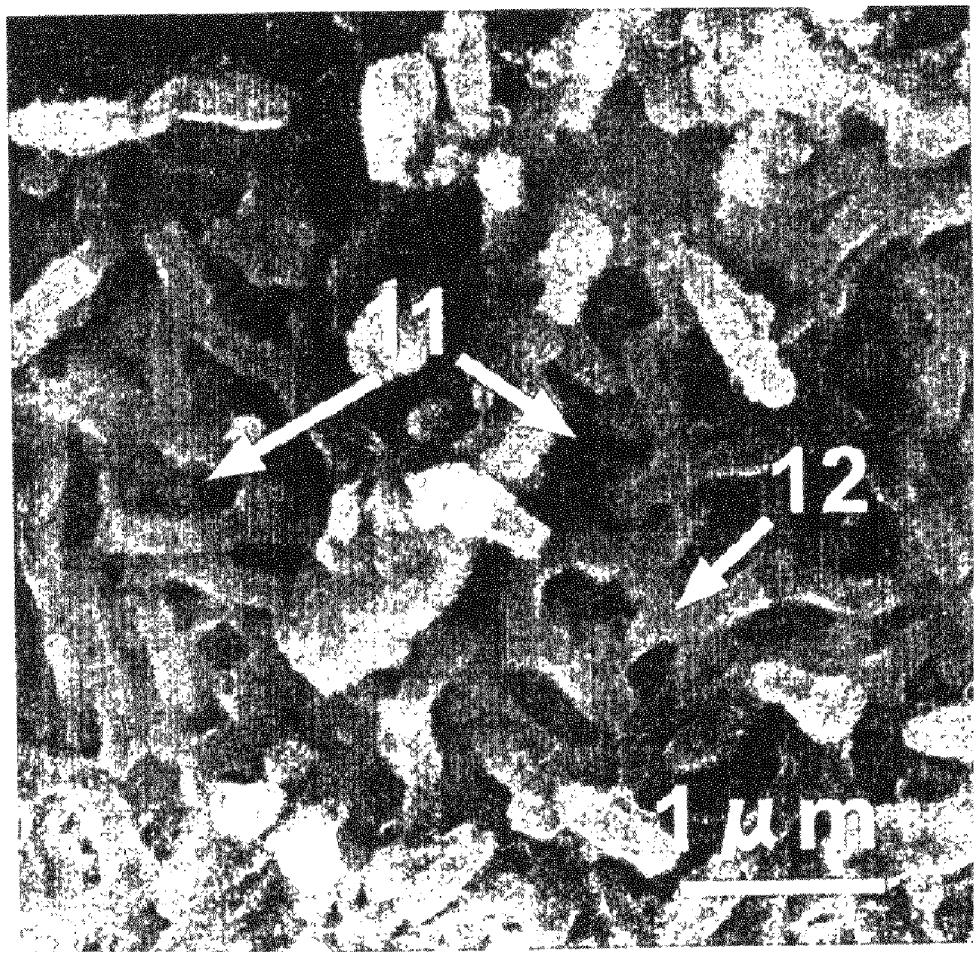

Next, an observation was carried out with a scanning electron microscope (SEM) to find that there was formed a rod-shaped structure having a large number of branches (a structure having a dendritic framework) as shown in FIGS. 2A and 2B.

In the voids in the branched rod-shaped structure (the voids in the framework), macropores of 300 to 500 nm or macropore-sized voids were found to be formed.

Figure 7:
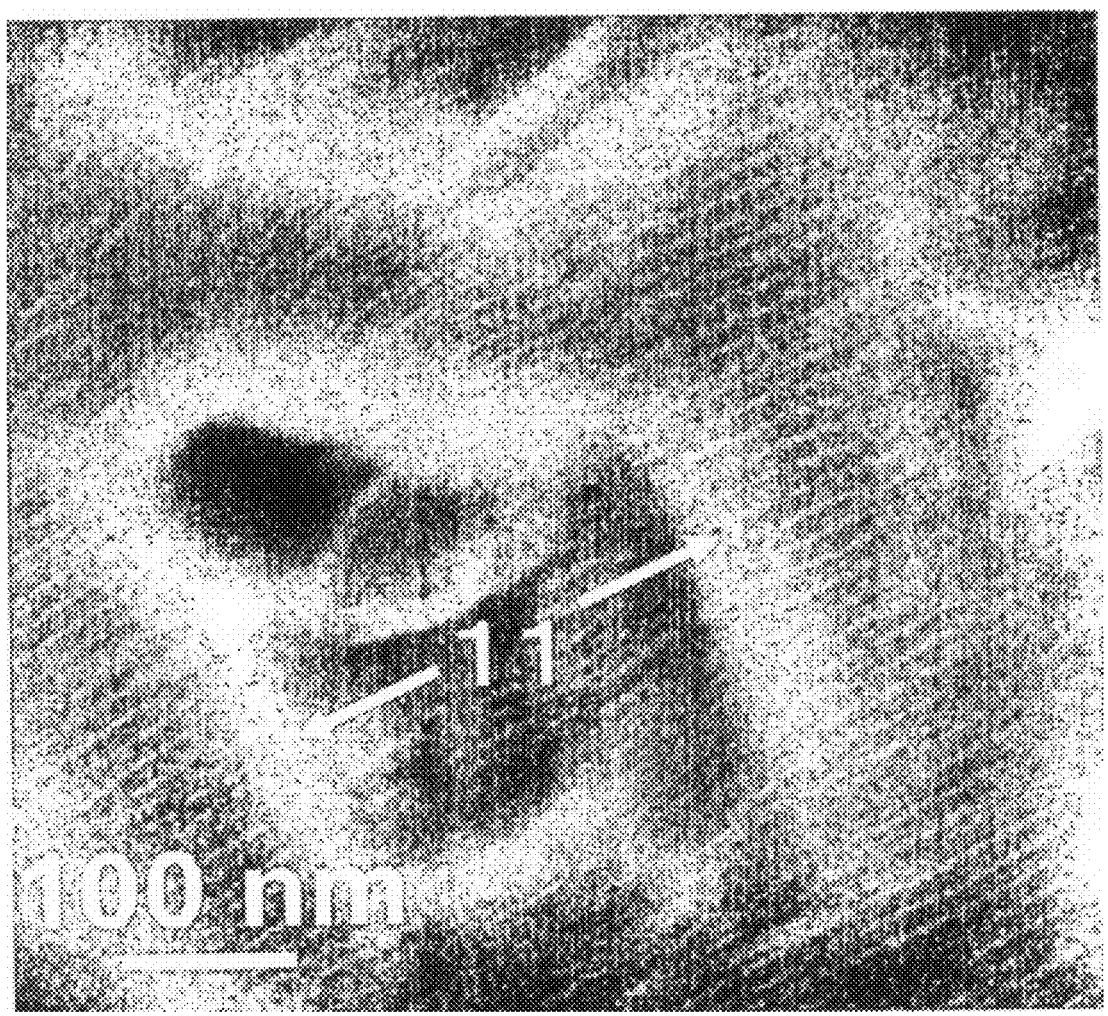
FIG. 7 is a photo of a structure according to the present invention as observed with a scanning electron microscope.
Figure 8:
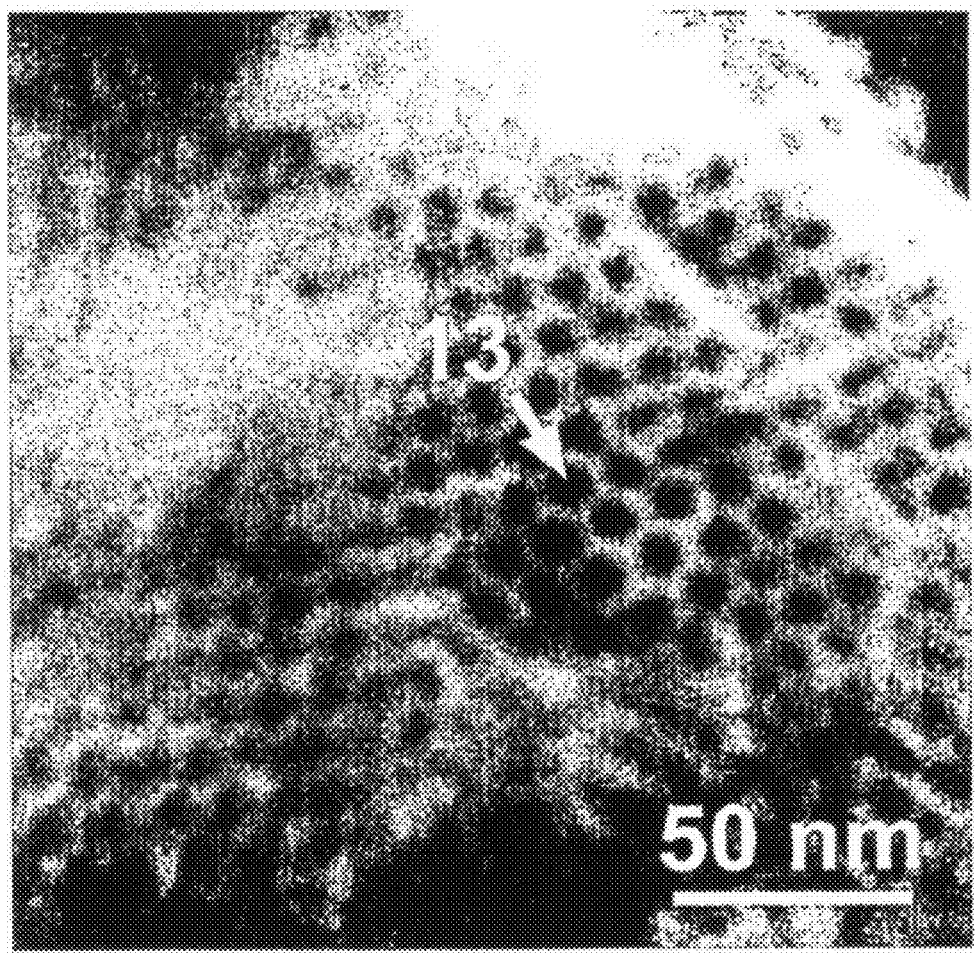
FIG. 8 is a photo of the mesopores of a structure according to the present invention as observed with a scanning electron microscope.

A SEM observation was carried out with a higher magnification, as shown in FIG. 7, a tubular mesopore of 14 nm in diameter was found to be oriented in the direction bisecting the longitudinal direction of the dendritic structure. In FIG. 7, reference numeral 11 denotes the pore size of a macropore formed by the dendritic framework. As shown in FIG. 8, in the section of the structure, there was formed a fine pore structure in which uniform tubular mesopores underwent honeycomb (,i.e. hexagonally symmetrical) packing. It is to be noted that the mesopore structure was not destroyed by the electron beam during the observation.

As described above, there was able to be synthesized a structure (hereinafter, referred to as a hierarchical structure, as the case may be) that had two types of fine pores different in pore size from each other, namely, macropores formed between the portions of the dendritic framework and mesopores formed in the framework.

Example 2

Horseradish peroxidase (hereinafter abbreviated as HRP; the mean diameter=4.8 nm, the isoelectric point (IEP)=7.2), a redox enzyme, was immobilized in the mesopores of the structure (mesoporous silica) produced in Example 1. Then, the resistance to organic solvent and the resistance to heat were measured. Further, the solution diffusivity was also studied.

(1) Enzyme Immobilization in Mesopores

A 5 mg/ml HRP solution was prepared by use of a 5 mM phosphate buffer solution (pH=7.4), and 10 mg of the synthesized mesoporous silica was added to 1 ml of the enzyme solution. The mixed solution was stirred with a shaker under the conditions of 4° C. and 20 hours, and thus, HRP was adsorbed in the fine pores of the mesoporous silica.

After completion of the reaction, the reaction solution was subjected to centrifugal separation at 4° C., for 10 minutes and at 20000 g, and the HRP-mesoporous silica precipitate was washed with purified water three times. The original enzyme solution and the supernatant liquid obtained were subjected to UV-V is absorbance measurement. The amount of HRP adsorbed to the mesoporous silica was derived from the concentration change between before and after adsorption by taking advantage of the absorption maximum of HRP at 403 nm. The enzyme-immobilized mesoporous silica after having been washed was subjected to vacuum freeze-drying for 10 hours to yield a powder sample. The adsorption amount of HRP was as high as 252 mg/g in relation to 1 g of the mesoporous silica. By varying the pH of the phosphate buffer solution, the adsorption amount of HRP was varied. From these results, HRP and the fine pores of the mesoporous silica conceivably interacted with each other electrostatically to immobilize HRP.

The introduction of HRP into the fine pores was confirmed by the fact that the nitrogen adsorption to the fine pores was decreased in the nitrogen adsorption measurement carried out for the mesoporous silica after the HRP adsorption.

(2) Resistance to Organic Solvent

For the purpose of evaluating the enzymatic activity, in an organic solvent, of the HRP immobilized in the mesoporous silica, there was used the oxidation reaction of 1,2-diaminobenzene in toluene in which t-butylhydroperoxide was used as an oxidizing agent.

A mixed solution was prepared by mixing 8 ml of a 50 mM anhydrous toluene solution of 1,2-diaminobenzene with 2 ml of a 1.1 M n-decane solution of t-butylhydroperoxide. To 1 ml of the mixed solution, 10 mg of the HRP-immobilized mesoporous silica was added, and the reaction was started at 37° C.; the 470-nm absorbance of 1,2-dinitrobenzene generated by the oxidation of 1,2-diaminobenzene was measured to follow the time variation. Thus, the enzymatic activity of HRP in toluene as solvent was determined.

Figure 9:
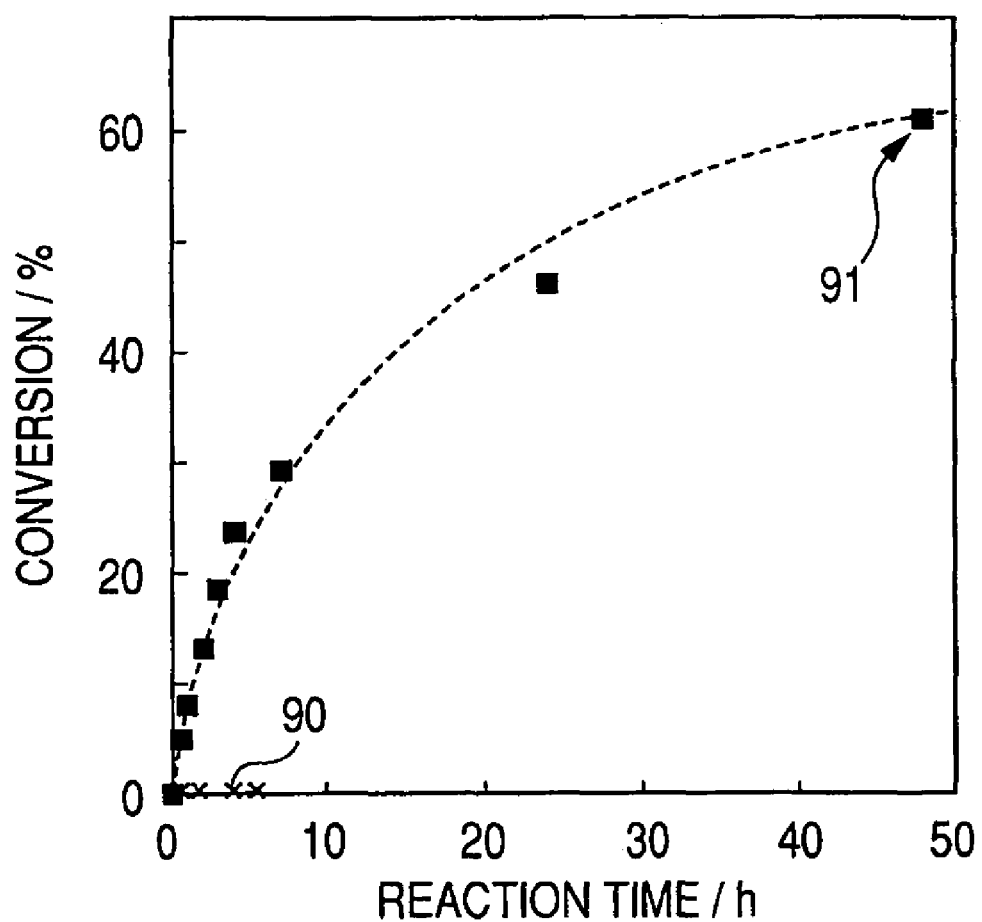
FIG. 9 is a graph showing the relation between the conversion ratio and the elapsed time when peroxidase was immobilized in the mesopores of a porous material produced in Example 1 and an enzymatic reaction was carried out in toluene.

As a comparative test, 0.5 mg of HRP itself was prepared, and the above described oxidation reaction was carried out, and the increase of the 470-nm absorbance was measured in the same manner as above. The results obtained are shown in FIG. 9. With HRP (free HRP) alone, no oxidation reaction in toluene occurred (plot 90), but with HRP immobilized in mesoporous silica, a very high activity was exhibited (plot 91). This is conceivably because HRP was denatured immediately after addition of HRP into toluene, and it was found that the immobilization of HRP in mesoporous silica attained a high stability.

(3) Resistance to Heat

Figure 10:
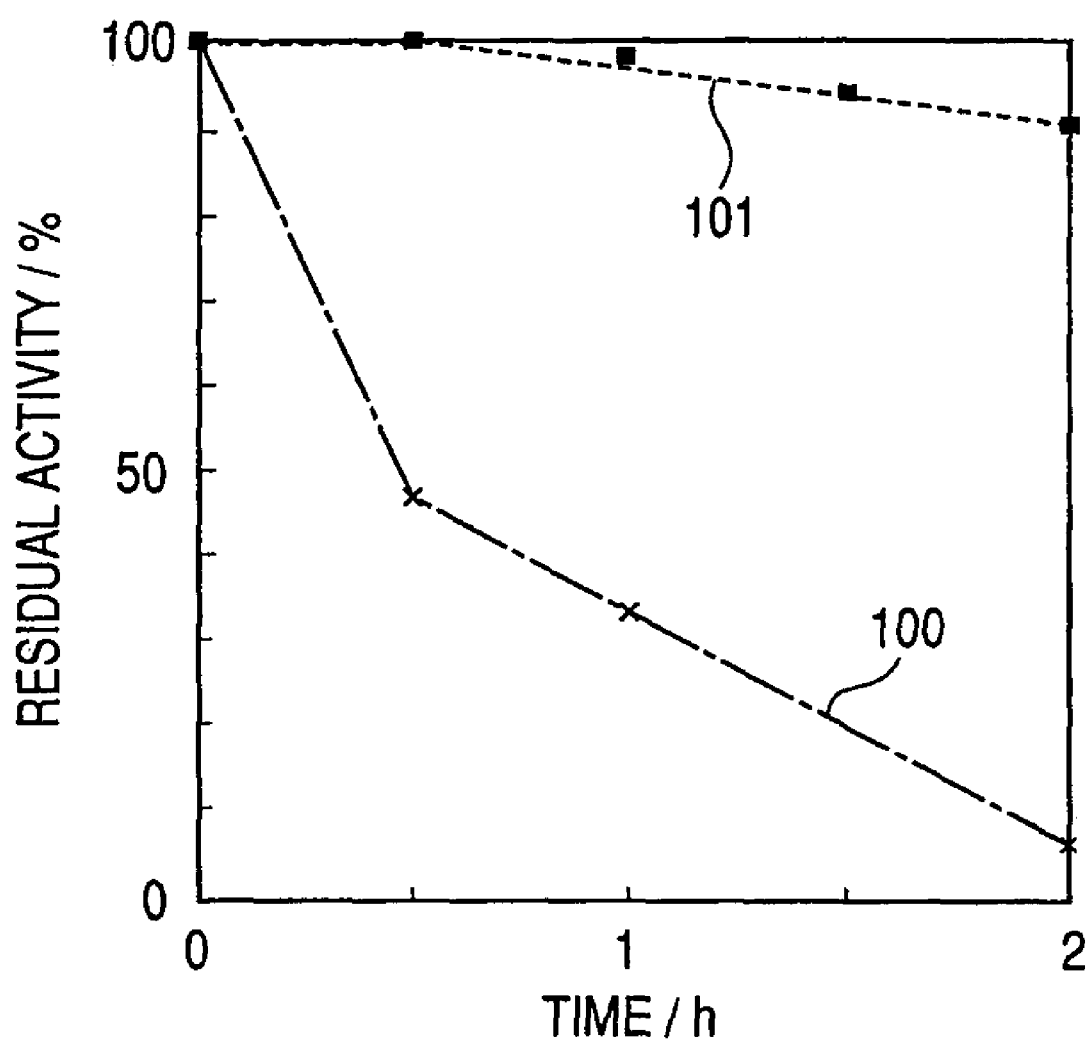
FIG. 10 is a graph showing the relation between the relative activity of an enzyme and the heat treatment time when peroxidase was immobilized in the mesopores of a porous material produced in Example 1 and a heat treatment was carried out at 70° C.

The HRP-immobilized mesoporous silica (plot 101) and usual non-immobilized HRP (plot 100) were heat treated in a phosphate buffer solution at 70° C. for 0 to 2 hours, and thereafter, the residual enzymatic activities thereof were measured; the results obtained are shown in FIG. 10. The thermal stability of the HRP immobilized in the mesoporous silica was determined by measuring the oxidative decomposition rate of phenol. For quantitative determination of phenol, the 4-aminoantipyrine calorimetric method was used.

To 10 mg of the HRP-immobilized mesoporous silica prepared by the above described HRP adsorption, 400 μl of a 50 mM sodium acetate buffer solution (pH=4.0) was added to prepare a solution; and the four same solutions thus prepared were heated at 70° C. respectively for 30, 60, 90 or 120 minutes. Each of the solutions was subjected to centrifugal separation and the HRP-immobilized silica was washed with purified water twice; then 400 μl of a 50 mM Tris-HCl (hydroxymethylaminomethane hydrochloride) buffer solution (pH=7.5), 8 μl of a 5000 ppm aqueous solution of phenol, and 2 μl of 3.0% hydrogen peroxide solution were added to the HRP-immobilized silica, and the reaction mixture thus obtained was allowed to react at 37° C. for 30 minutes; after centrifugal separation, 150 μl of the supernatant liquid was added, and 150 μl of 1% hexacyanoferrate and 300 μl of 1% 4-aminoantipyrine, both prepared with a 1 M aqueous solution of glycine (pH=9.6) were added, and the mixture was stirred; and thereafter, the absorbance at around 500 nm was measured promptly.

The enzymatic activity of the non-immobilized HPR was reduced by half by heat treatment at 70° C. for 30 minutes, and was only about 10% of the initial enzymatic activity after 2 hours. On the contrary, the HRP-immobilized mesoporous silica was verified to have a high stabilization effect against heat; 90% or more of the enzymatic activity survived after a heat treatment at 70° C. for 2 hours.

Figure 11:
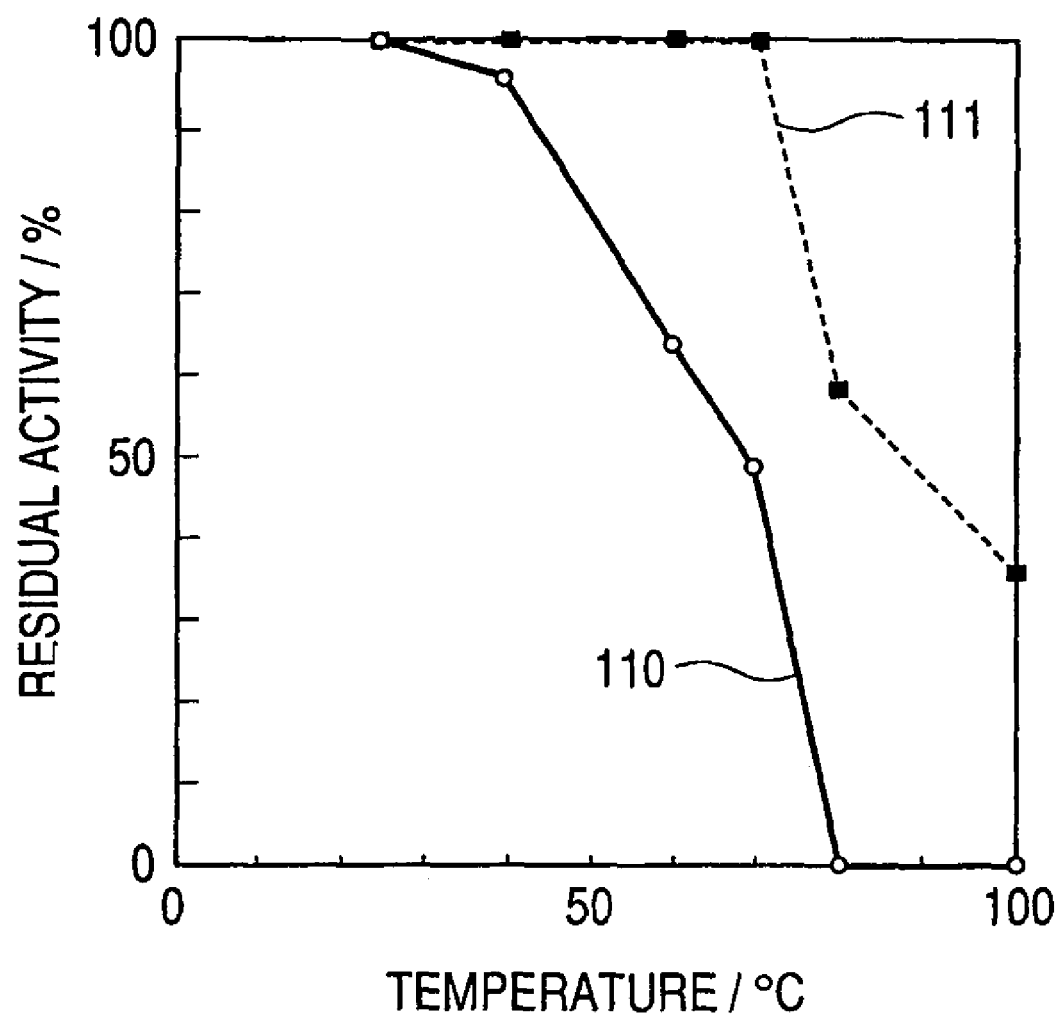
FIG. 11 is a graph showing the temperature dependence of the relative activity when peroxidase was immobilized in the mesopores of a porous material produced in Example 1 and a heat treatment was carried out at predetermined temperatures for 30 minutes.

FIG. 11 shows the results of the temperature dependence measurement of HRP on the basis of the phenol oxidation reaction. Each of the HRP (plot 110) and the immobilized HRP (plot 111) was preliminarily treated at 25° C. to 100° C. for 30 minutes, and thereafter the enzymatic activity was measured. The remaining activity of the usual HRP was 0% under the conditions of 70° C. and 30 minutes, but the HPR immobilized in the hierarchical mesoporous silica exhibited a 50% or more activity under the same conditions, and held an about 40% of the enzymatic activity even after the treatment at 100° C. without going down to 0%.

(4) Solution Diffusivity

Next, there was made a study of how the internal diffusion of the adsorbed material was varied by the presence of the macropores or macropore-sized voids between the adjacent portions of the framework. Specifically, a hierarchical porous material prepared according to the present invention and a monodisperse mesoporous material having no macropores were synthesized, and these materials were compacted into disc-shaped pellets, and the HRP adsorption behavior of each of these materials was studied.

Each of the calcined powder of a hierarchical porous silica synthesized according to the above described synthesis method and the calcined powder of a monodisperse mesoporous silica having no macropores (the particles of Non-patent document 1) was weighed out in an amount of 0.2 g. Each of the weighed material was compacted into a disc-shaped pellet of 15 mm in diameter and 1 mm in thickness by means of a tablet forming press.

A 5 mg/ml HRP solution was prepared by use of a 5 mM phosphate buffer solution (pH=7.4), and each of the pellet-shaped mesoporous silicas was placed in 5 ml of the HRP solution. Each of the mixed solutions was slowly shaken at 4° C. for 48 hours with a shaker, HRP was thereby adsorbed to each of the mesoporous silicas, and the time variation of the adsorption amount in each of the HRP solutions was measured from the absorption intensity variation at the 403 nm of the HRP solution. The hierarchical mesoporous silica exhibited a relative adsorption amount of 80% or more at an elapse time of about 1 hour from the start of the adsorption. The adsorption amount was approximately the same as the adsorption amount of the calcined powder before compacting.

However, the mesoporous material that had neither dendritic framework nor macropores exhibited a drastic decrease of the adsorption rate by compacting into pellet. The present inventors interpret that these results were caused by the fact that the hierarchical mesoporous material of the present invention maintained the macropores even in the compacted pellet, so that a high internal diffusion rate was maintained. On the other hand, in the mesoporous material having no dendritic framework, the compacting made the material itself too higher in density, so that the adsorption rate was conceivably decreased.

Comparative Example 1

Enzyme Immobilization to Mesopores

As a comparative example, SBA-15 in which tubular fine pores were formed in parallel with the long axis direction of rod-shaped particles was synthesized, and the HRP adsorption and the stabilization effect in an organic solvent were measured. The synthesis method of SBA-15 is described in Science, No. 279, p. 548.

The synthesized SBA-15 was evaluated by the X-ray diffraction method, and consequently, there was identified a diffraction peak to be assigned to the (100) plane of a hexagonal structure with an interplanar distance of 9.8 nm. From the nitrogen adsorption isotherm measurement, the synthesized SBA-15 was found to have a specific surface area of 800 $m^2/g$ and a fine pore size of 7.4 nm.

The synthesized SBA-15 was subjected to the same HRP adsorption experiment as in Example 1. The adsorption amount of HRP was found to be 25 mg/g, exhibiting a very small adsorption amount that was $\frac{1}{10}$ or less times the adsorption amount in the hierarchical mesoporous silica synthesized by the present inventors. From the analysis of the nitrogen adsorption isotherm for the sample after the HRP adsorption, the fine pore volume of SBA-15 was found not to be decreased from before to after the HRP adsorption, and HRP was found to be little adsorbed in the fine pores of SBA-15.

Next, the time-dependent adsorption amount of HRP in each mesoporous silica was measured, and consequently it was found that the time to reach the saturated adsorption amount was very short in the hierarchical mesoporous silica having macropores according to the present invention.

Comparative Example 2

Resistance to Organic Solvent

Also by use of SBA-15, the organic solvent stability of HRP was measured by means of the above described method to be compared with the hierarchical mesoporous silica according to the present invention. There was observed only a slight enzymatic activity due to the HRP immobilized to SBA-15. However, with the HRP immobilized to SBA-15, the reaction product, 1,2-dinitrobenzene, was gradually identified after the start of the reaction. On the contrary, in the hierarchical mesoporous silica, 1,2-dinitrobenzene was identified in an amount of 10 or more times the amount found in SBA-15, from immediately after the start of the reaction.

In this connection, in SBA-15, tubular fine pores were formed in parallel with the long axis direction of the rod-shaped particles; consequently, the aspect ratios of the tubular fine pores were large, so that the diffusion of HRP or a substrate from the outside into the interior of the fine pores and from the interior of the fine pores to the outside was made poor; and the number of the fine pore openings on the surface was small. Consequently, the introduction of HRP or the substrate was made slow. From these results, it has been revealed that the hierarchical mesoporous silica synthesized by the present inventors is excellent in the internal diffusion of a protein or a substrate and excellent as a support for biological materials and the like because the hierarchical mesoporous silica has macropores and the like.

Example 3

This Example is a case in which the surface of the hierarchical mesoporous silica produced in Example 1 was modified with an oxide of zirconium, glucose oxidase (abbreviated as GOD, diameter=8.0 nm, IEP=4.6) that is a redox enzyme was immobilized, and the stability against heat was measured.

To 90 ml of purified water, 10 g of zirconium oxynitrate dihydrate was added and dissolved at room temperature to prepare a 10% by weight aqueous solution of zirconium oxynitrate. To this solution, the hierarchical mesoporous silica synthesized in Example 1 was added and soaked for 20 hours. Thereafter, the supernatant was removed from the mixture by means of centrifugal separation, and the mixture was washed with water and dried at room temperature.

The hierarchical mesoporous silica modified with zirconium was evaluated by the X-ray diffraction method, and consequently, almost the same diffraction pattern as before modification was found to be exhibited, verifying that the periodic structure of the mesopores was not destroyed. The chemical bonding state of the silica surface was measured by X-ray photoelectron spectrometry (XPS), and consequently, a peak ascribable to Zr—O was identified, verifying that a zirconium oxide layer was formed on the silica surface.

Subsequently, GOD was immobilized in the fine pores of the hierarchical mesoporous silica having been modified with zirconium, and the stabilization effect was measured on the basis of the oxidation decomposition reaction of phenol.

A 5 mg/ml solution of GOD was prepared by use of a 5 mM phosphate buffer solution (pH=5.0), and to 1 ml of the GOD solution, 10 mg of the hierarchical mesoporous silica modified with zirconium was added. The mixed solution was stirred with a shaker under the conditions of 4° C. and 20 hours to immobilize GOD in the fine pores of the mesoporous silica. After adsorption, the reaction solution was subjected to centrifugal separation at 4° C., for 10 minutes and at 20000 g, to yield a GOD-immobilized silica. From the 280-nm absorption maximum values in the supernatant solution before and after the GOD immobilization, the amount of GOD adsorbed to the mesoporous silica was derived. The adsorption amount of GOD was 120 mg/g or more. The presence of the enzyme molecules introduced into the fine pores was identified with a nitrogen adsorption measurement apparatus from the decrease of the adsorption amount in the fine pores. GOD was little adsorbed to the mesoporous silica that was not modified with zirconium.

To 10 mg of each of the GOD-immobilized mesoporous silica and the GOD-immobilized SBA-15 prepared by the above described GOD adsorption, 400 μl of a 50 mM sodium acetate buffer solution (pH=4.0) was added to prepare a solution; and the four same solutions of each of the above described GOD-immobilized substances thus prepared were heated at 70° C. respectively for 30, 60, 90 or 120 minutes. After heating, each of the solutions was subjected to centrifugal separation and the GOD-immobilized silica was washed with purified water twice; then 400 μl of the 50 mM Tris-HCl buffer solution (pH=7.5), 100 μl of a 10% aqueous solution of β-D-glucose, 8 μl of a 5000 ppm aqueous solution of phenol, and 100 μl of a 100 μ/ml HRP solution were added to the GOD-immobilized silica, and the reaction mixture thus obtained was allowed to react at 37° C. for 30 minutes; after centrifugal separation, the absorbance at around 500 nm was measured in the same manner as in Example 2.

The relative activity of the non-immobilized GOD was reduced down to 0% by heat treatment at 70° C. for 30 minutes. On the contrary, the GOD immobilized in mesoporous silica was verified to have a high stabilization effect against heat; 70% or more of the enzymatic activity survived after a heat treatment at 70° C. for 120 minutes.

The time variation of the decomposition of phenol at 37° C. was measured by using the GOD-immobilized hierarchical mesoporous silica that was not subjected to heat treatment.

To 10 mg of the GOD-immobilized mesoporous silica prepared by the above described GOD adsorption, 400 μl of the 50 mM Tris-HCl buffer solution (pH=7.5) and 100 μl of an aqueous solution of β-D-glucose were added, and further, 8 μl of an 5000 ppm aqueous solution of phenol and 100 μl of a 100 μ/ml HRP solution were added. The thus prepared solution was allowed to react at 37° C. for a predetermined time. After centrifugal separation, the absorbance at around 500 nm was measured in the same manner as in Example 2. Form the results thus obtained, the relative activity for the phenol decomposition concentration after 30 minutes was derived. The GOD immobilized in the hierarchical mesoporous silica exhibited a 100% relative activity for a reaction for 5 minutes.

From these results, it was revealed that the hierarchical mesoporous silica having macropores was provided with a high internal diffusion due to the macropores thereof, and simultaneously, the enzyme immobilized in the mesopores attained a high stabilization effect.

In the same manner as in Example 1, GOD adsorption experiments were carried out by using the pellet-shaped hierarchical mesoporous silica and the pellet-shaped monodisperse mesoporous silica having no macropores. Each of these pellets was soaked in the aqueous solution of zirconium oxynitrate according to the above described method to be subjected to zirconium treatment, and then the time dependent adsorption behavior of GOD was measured. In the same manner as in Example 1, the pellet-shaped hierarchical mesoporous silica according to the present invention exhibited no variation in adsorption behavior as compared to the powder before compacting. However, GOD was little adsorbed to the pellets of the monodisperse mesoporous silica having no macropores. This is conceivably because in the pellet-shaped monodisperse mesoporous silica, the particles thereof were densely packed to deaccelerate the internal diffusion, resulting in an insufficient diffusion of GOD in the mesopores.

Example 4

This Example is a case in which the surface of the hierarchical mesoporous silica synthesized in Example 1 was modified with a silane coupling agent, and α-amylase was immobilized on the silica surface by covalent bonding.

To 50 ml of a 10% (v/v) toluene solution of 3-aminopropyltriethoxysilane, 1.0 g of the hierarchical mesoporous silica synthesized in Example 1 was added, and the solution thus obtained was stirred in an atmosphere of nitrogen at 120° C. for 48 hours. After the reaction, the precipitate was filtered out, washed with toluene, methanol and dichloromethane, and dried at room temperature.

Next, 1.0 g of the thus dried sample was dissolved in a 25 ml of a 2.5% glutaraldehyde solution prepared by use of a phosphate buffer solution (pH=6.6), and stirred at room temperature for 1 hour. The obtained precipitate was washed with purified water four or more times, and thereafter dried at room temperature.

The hierarchical mesoporous silica modified with glutaraldehyde was evaluated by the X-ray diffraction method, and consequently, almost the same diffraction pattern as before modification was found to be exhibited, verifying that the mesopore structure was not destroyed. The identification of the functional groups introduced onto the silica surface was carried out by means of FT-IR, and consequently, peaks ascribable to R—CH=N, C=O and —CHO were identified, verifying that $Si(CH_2)_3N=CH(CH_2)_3CHO$ was covalently bonded to the silica surface.

Subsequently, α-amylase was immobilized in the fine pores of the hierarchical mesoporous silica having been modified, and the stabilization effect was measured on the basis of the hydrolysis reaction of starch to maltose.

A 1 mg/ml solution of α-amylase was prepared by use a 50 mM phosphate buffer solution (pH=6.0), and in 1 ml of this solution, there was added 0.2 g of the hierarchical mesoporous silica synthesized and modified according to the above described methods, and compacted into pellets in the same manner as in Example 1. The mixed solution was soaked under the conditions of 4° C. and 20 hours with a shaker to adsorb α-amylase in the fine pores of the mesoporous silica. After completion of the reaction, the pellets were filtered out, and washed with purified water three times. The original enzyme solution and the supernatant liquid were subjected to UV-Vis absorbance measurement. By using the 280-nm absorption maximum of α-amylase, the amount of adsorption to the mesoporous silica was derived from the concentration variation from before to after the adsorption. The amount of the adsorbed α-amylase was as high as 140 mg/g. The adsorption experiments of α-amylase to the powdery hierarchical mesoporous silica subjected to no surface modification and the compacted pellet-shaped monodisperse mesoporous silica under the same conditions little showed adsorption behavior. Consequently, it is conceivable that owing to the high internal diffusion due to the macropores, α-amylase was immobilized onto the silica surface through the bonding between the —CHO modifying the silica surface and the —$NH_2$ of α-amylase.

Subsequently, the pellet-shaped amylase-immobilized mesoporous silica and the non-immobilized amylase were subjected to heat treatment at 25° C. to 70° C. in a sodium acetate buffer solution, and then subjected to enzymatic activity measurement.

To 10 mg of the above described amylase-immobilized mesoporous silica, 400 µl of a 50 mM sodium acetate buffer solution (pH=5.0) was added to prepare a solution; and the solutions thus prepared were heat treated at 25° C. to 70° C., respectively, for 30 minutes. After heating, each of the solutions was subjected to centrifugal separation, and the amylase-immobilized silica was washed with purified water twice. By use of the same 50 mM sodium acetate buffer solution, a 0.125% soluble starch solution was prepared, and 300 µl of the starch solution was added to the amylase-immobilized silica after washing, and the mixture was allowed to react at 40° C. for 15 minutes. After termination of the reaction, the supernatant was obtained by centrifugal separation, 1 ml of 0.5 N acetic acid and 3 ml of an iodine-potassium solution (0.015% iodine-0.15% potassium iodide solution) were added to this supernatant solution, and the supernatant solution was stirred sufficiently and then subjected to measurement of the 700-nm absorbance maximum. Usual α-amylase exhibited a relative activity of 20% under the conditions of 60° C. and 30 minutes, but α-amylase immobilized in the hierarchical mesoporous silica exhibited a relative activity of 90% or more under the same conditions to verify the stabilization effect.

Example 5

This Example is a case in which a single strand DNA was introduced onto the mesopore surface of the hierarchical mesoporous silica produced in Example 1. This Example is an example of biosensing element that optically detects a specific reaction between single strand DNAs by taking advantage of hybridization reactions, FIG. 12 being a schematic view illustrating an example of the configuration of a biosensing element.

Hybridization means the formation of a nucleic acid hybrid or the nucleic acid molecule hybridization, and is used as a method for investigating the primary structure homology of a nucleic acid, namely, the base sequence homology or a method for detecting nucleic acids having a homologous base sequence. Hybridization takes advantage of the property that two single-stranded nucleic acids mutually form hydrogen bonds between the complementary base pairs (A-T, G-C) to form a double helix double stranded nucleic acid.

The hierarchical mesoporous silica synthesized in Example 1 and the SBA-15 used in Comparative Example 1 were soaked for 1 hour in a 10% solution of 3-aminopropyl-triethoxysilane in 95% aqueous ethanol, and then unreacted solution was removed with a centrifugal separator. After washing with ethanol, the reaction was allowed to proceed in an atmosphere of nitrogen at 120° C. for 1 hour, to introduce amino groups onto the pore surface of the mesoporous silica.

Further, the amino group-introduced hierarchical mesoporous silica was soaked in a 1 mM dimethyl sulfoxide solution of GMBS for 2 hours, and then washed with dimethyl sulfoxide to introduce maleimide groups onto the pore surface of the mesoporous silica. The introduction of these functional groups was identified by means of FT-IR.

A DNA probe having thiol groups introduced therein was synthesized by use of a DNA automatic synthesizer, and thereafter the DNA probe was purified by high performance liquid chromatography.

DNA probe: HS—$(HS_2)_6$—O—$PO_2$—O-5'-SEQ ID NO:1 -3'

Then, 10 µl of a 2 µM solution of the synthesized and purified DNA probe, 40 µl of HEPES buffer solution (N-2-hydroxyethylpiperazine-N'-2-ethane sulfonic acid; 10 mM, pH=6.5) and 50 µl of an additive (ethylene glycol) were mixed together to prepare a reaction solution. The mixed solution was added to the hierarchical mesoporous silica having maleimide groups introduced therein, the mixture thus obtained was allowed to stand at room temperature for 2 hours, and the single strand DNA was thereby immobilized onto the surface of the mesoporous silica.

Figure 12:
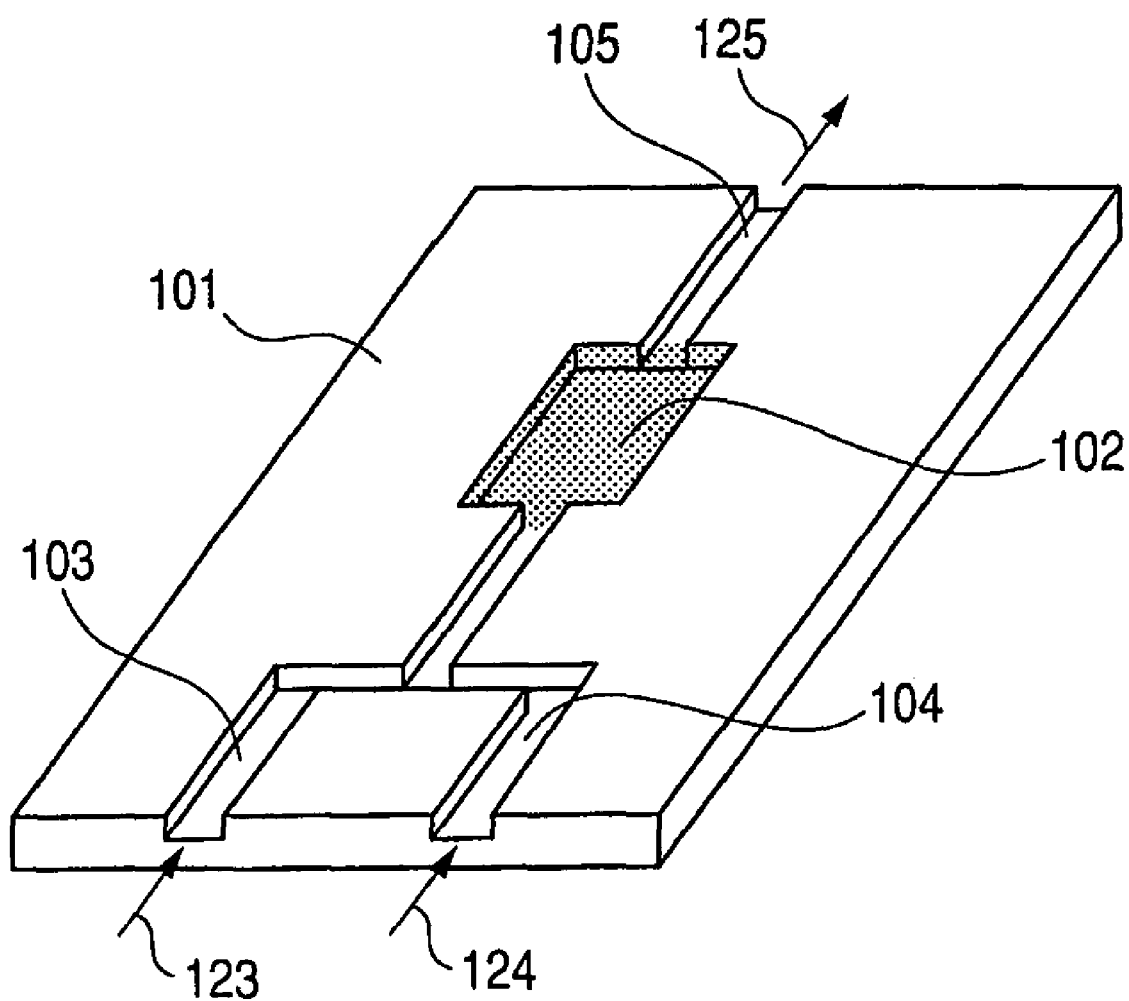
FIG. 12 is a schematic view illustrating a case where a structure according to the present invention is applied as a biosensing element.

The DNA probe-immobilized mesoporous silica was filled in the groove on the chip substrate shown in FIG. 12, and other channels were disposed as shown in FIG. 12, and thus a biosensing element was fabricated. In this figure, reference numeral 101 denotes a substrate, and 102 denotes the DNA probe-immobilized hierarchical mesoporous silica prepared according to present Example. Reference numerals 103 and 104 each denote a solution introduction tube, and 105 denotes a solution discharge tube for the solutions having been introduced.

By use of an automatic DNA synthesizer, there was synthesized a DNA target that had a base sequence complementary to the DNA probe and the 5' terminal thereof was fluorescence labeled with Texas Red. Then, 80 µl of a 0.1 µM solution of the DNA target, 17 µl of 20×SSC (0.3 M sodium citrate, 3.0 M sodium chloride) and 3 µl of a 10% aqueous solution of sodium dodecyl sulfate were mixed together. The hybridization solution thus prepared by mixing was introduced in the direction indicated by an arrow 123 through the solution introduction tube 103 shown in FIG. 12. After a predetermined time of staying in a stationary state, the solution was discharged from the solution discharge tube 105 in the direction indicated by an arrow 125.

After a predetermined time of the hybridization reaction, a hundredfold diluted solution of 20×SSC was injected as a washing solution from the washing solution introduction tube 104 in the direction indicated by an arrow 124, and washing was carried out. Then, by use of a scanner for microarray, the fluorescence intensity (hybridization signal) of the DNA probe-immobilized portion and the fluorescence intensity (background signal) of the sample having no DNA probe immobilized therein were measured.

The DNA probe-immobilized SBA-15 was small in the hybridization signal and was not able to attain a high fluorescence intensity ratio (hybridization signal/background signal); the time variation of the fluorescence intensity due to the hybridization reaction was measured, and the time to reach the saturated intensity was also found to be long. On the contrary, the DNA probe-immobilized hierarchical mesoporous silica perfected the hybridization reaction in a very short time, and attained an excellent fluorescence intensity ratio. These results are conceivably understood as follows: the high adsorption amount of the DNA probe in the mesopores of the hierarchical mesoporous silica increased the fluorescence signal and the excellent internal diffusion due to the macropores led to the completion of the hybridization reaction in a short time.

In present Example, from the above described results, it has been verified that by using the hierarchical mesoporous silica in which the above described biological material has been immobilized, a biosensing element capable of performing a high sensitivity detection in a short time can be fabricated.

Example 6

In this example, in the fine pores of the hierarchical mesoporous silica synthesized in Example 1, a mouse monoclonal antibody (the antigen was a human serum albumin) was immobilized, and the detection and the measurements of a target material was carried out by taking advantage of a specific bonding reaction between the antigen and the antibody.

To each of 10 mg of the hierarchical mesoporous silica synthesized in Example 1 and 10 mg of the SBA-15 used in Comparative Example 1, there was added 10 ml of a 1 mg/ml aqueous solution of the mouse monoclonal Fab type antibody prepared with purified water. Each of the solutions thus prepared was stirred at 4° C. for 6 hours, to immobilize the antibody in the mesopores of the mesoporous silica, and then washed with purified water three times. To the antibody-immobilized mesoporous silica, a solution of a horse radish peroxidase-labeled human serum albumin (abbreviated as HRP-HSA) solution was added, and the mixture was allowed to react at room temperature for a predetermined time (1 to 4 hours). In order to remove the nonspecifically adsorbed HRP-HSA, the antigen-antibody-immobilized mesoporous silica was washed with purified water a few times, then subjected to vacuum freeze-drying, and the dried sample was allowed to stand at 37° C. for an optional period of time. Then, to the sample, 400 µl of a 50 mM Tris-HCl (pH=7.5), 8 µl of a 5000 ppm aqueous solution of phenol and 2 µl of a 30% hydrogen peroxide solution were added, and the mixture was allowed to react at 37° C. for 30 minutes. After centrifugal separation, the absorbance at around 500 nm was measured in the same manner as in Example 2, and thus there was measured the enzymatic activity of the HRP labeled with the HSA specifically bonded to the immobilized antibody.

Additionally, to the hierarchical mesoporous silica, a nonspecific mouse immunoglobulin antibody (mouse Ig) that was not an antibody to the HRP-HSA was immobilized in the same manner as described above. Then, according to the above described procedures, there was measured the absorbance difference between the case where the antibody specifically bonded to the HSA was used and the case where the nonspecific antibody was used. Consequently, the nonspecific mouse Ig was found to be obviously smaller in the HRP activity than the mouse monoclonal Fab-type antibody-immobilized mesoporous silica according to present Example. From these results, it was verified that the antibody was immobilized in the mesoporous silica, and the antigen-antibody reaction occurred in the fine pores even after the immobilization of the antibody in the mesoporous silica.

To the above described antibody-immobilized mesoporous silica, a HRP-HSA solution was added, and the mixture was allowed to react at room temperature for a predetermined time (1 to 4 hours), and thus the time variation of the antigen-antibody reaction was measured. Consequently, as verified in Examples 2, 3 and 4, a high antigen-antibody reaction rate was identified only in the case where the hierarchical mesoporous silica was used. This is conceivably because the external environmental effect denatured the HRP-HSA that was not immobilized in the fine pores such as the HRP-HSA adsorbed to the outside of the fine pores through nonspecific adsorption, and thus the HRP-HSA was not stabilized.

The antibody-immobilized mesoporous silica obtained in the above and the nonimmobilized mouse monoclonal antibody powder each were stored in a dried state at 37° C. for 3 weeks and each were subjected to a time variation measurement of the HRP activity due to the antigen-antibody reaction. The bonding activity of each of the above silica and powder immediately before the start of the storage in a dried state at 37° C. was defined as 100. The nonimmobilized mouse monoclonal antibody became zero in relative activity after one week to be completely deactivated. On the other hand, the antigen-antibody reaction of the mouse monoclonal antibody immobilized in the hierarchical mesoporous silica exhibited a relative activity of 90% or more even after three weeks.

Example 7

This Example is a case in which the same hierarchical mesoporous silica as synthesized in Example 1 was synthesized on an electrode, further glucose oxidase (GOD) and a mediator were immobilized in the mesopores, and the glucose concentration was measured. As the electrodes, a carbon electrode and a platinum electrode were used.

In 76.5 ml of purified water, 2.40 g of a triblock copolymer $(EO_{20}PO_{70}EO_{20}; HO(CH_2CH_2O)_{20}(CH_2CH(CH_3)O)_{70}(CH_2CH_2O)_{20}H)$ was dissolved. Further, the aqueous solution obtained was added with 7.5 ml of 36% by weight of concentrated hydrochloric acid, and stirred at room temperature for 30 minutes. Then, the aqueous solution was added with 13.9 g of n-decane, and was stirred at room temperature for 2 hours. Further, this mixed solution was added with 0.027 g of $NH_4F$ as a hydrolysis catalyst and 5.10 g of tetraethoxysilane (TEOS) to prepare a precursor solution. The final composition (in molar ratio) of the precursor solution was made to satisfy the following ratio: TEOS:HCl: $EO_{20}PO_{70}EO_{20}$:$NH_4F$:n-decane=25:90:0.4:0.7:100.

The precursor solution was stirred at 40° C. for 20 hours, and then allowed to react at 120° C. for 48 hours. The white precipitate thus obtained was washed with purified water sufficiently. The white precipitate was appropriately added with ethanol, and subjected to centrifugal separation at 3000 rpm to 6000 rpm, to yield a paste-like hierarchical mesoporous silica. The obtained sample was coated onto a carbon electrode, dried at room temperature, calcined in air at 500° C. to decompose and remove the surfactant from inside the fine pores to synthesize the hierarchical mesoporous silica on the carbon electrode.

The mesoporous silica powder sampled from the electrode was evaluated by means of the X-ray diffraction method, and consequently there were identified a diffraction peak to be assigned to the (100) plane, and also diffraction peaks to be assigned to the (110), (200) and (210) planes of a hexagonal structure, in the same manner as in Example 1.

A 5 mg/ml GOD solution was prepared by use of a 5 mM sodium acetate buffer solution (pH=7.4); and the synthesized mesoporous silica carbon electrode was soaked in 10 ml of the enzyme solution. The solution was slowly stirred with a shaker under the conditions of 4° C. and 20 hours, and thus, GOD was adsorbed in the fine pores of the mesoporous silica on the electrode. The GOD-mesoporous silica on the electrode was washed with purified water three times to yield a GOD-immobilized electrode. From the 280-nm absorption maximum values in the supernatant solution before and after the GOD immobilization, the amount of GOD adsorbed to the mesoporous silica was derived by subtracting the adsorption only to the carbon electrode as the background. The adsorption amount of GOD was 230 mg/g or more. After drying the sample, for the purpose of supporting the mediator in the mesopores, the sample was made to stay in a stationary state at room temperature for 12 hours in 100 ml of a 100 mM solution of potassium ferricyanate prepared with 50 ml of MOPS buffer solution. After soaking, centrifugal separation and washing with purified water were carried out, and dried at room temperature to yield a GOD electrode for measuring glucose.

Figure 13:
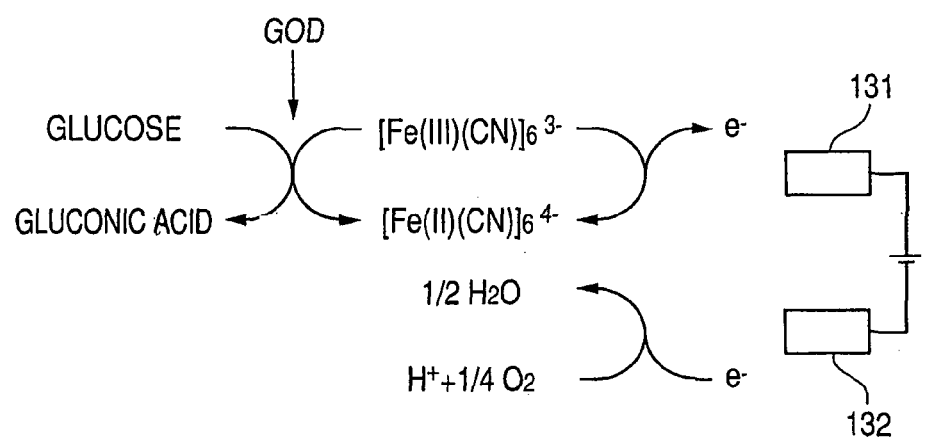
FIG. 13 is a diagram illustrating a reaction mechanism in which a structure according to the present invention can be applied as a biosensing element.

By taking advantage of the reaction mechanism shown in FIG. 13, the concentration of glucose is measured. By taking advantage of the mechanism, the blood sugar level in blood or the like can be measured. Specifically, when the glucose in blood reaches the sensor, the glucose and GOD react with each other, and at the time of the reaction, the glucose releases electrons to be converted into gluconic acid. The electrons released from the glucose are trapped by the ferricyan ion ($[Fe(III)(CN)_6]^{3-}$). The ferricyan ion ($[Fe(III)(CN)_6]^{3-}$) having trapped an electron is converted into the ferrocyan ion ($[Fe(II)(CN)_6]^{4-}$). A working electrode 131 detects whether the reaction is occurring or not. An electric voltage is applied to the working electrode in advance, the counter electrode 132 does not accept the electron of the ferrocyan ion ($[Fe(II)(CN)_6]^{4-}$), but the hydrogen ion ($H^+$) accepts the electron on the counter electrode to generate water ($H_2O$) in cooperation with oxygen ($O_2$). By measuring the electric current value at this time, the amount of glucose is derived and the blood sugar level can be determined.

Figure 14:
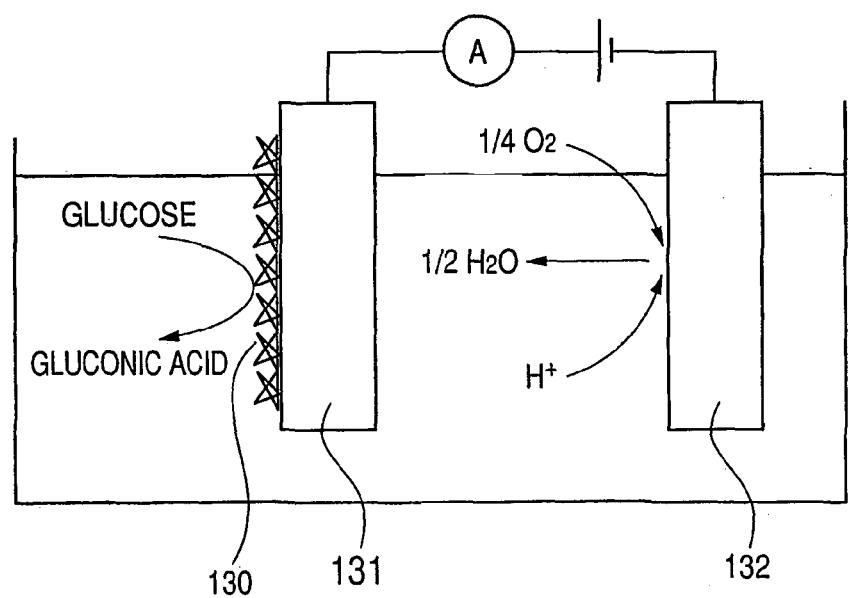
FIG. 14 is a schematic view illustrating a case where a structure according to the present invention is applied as a biosensing element.
Figure 15:
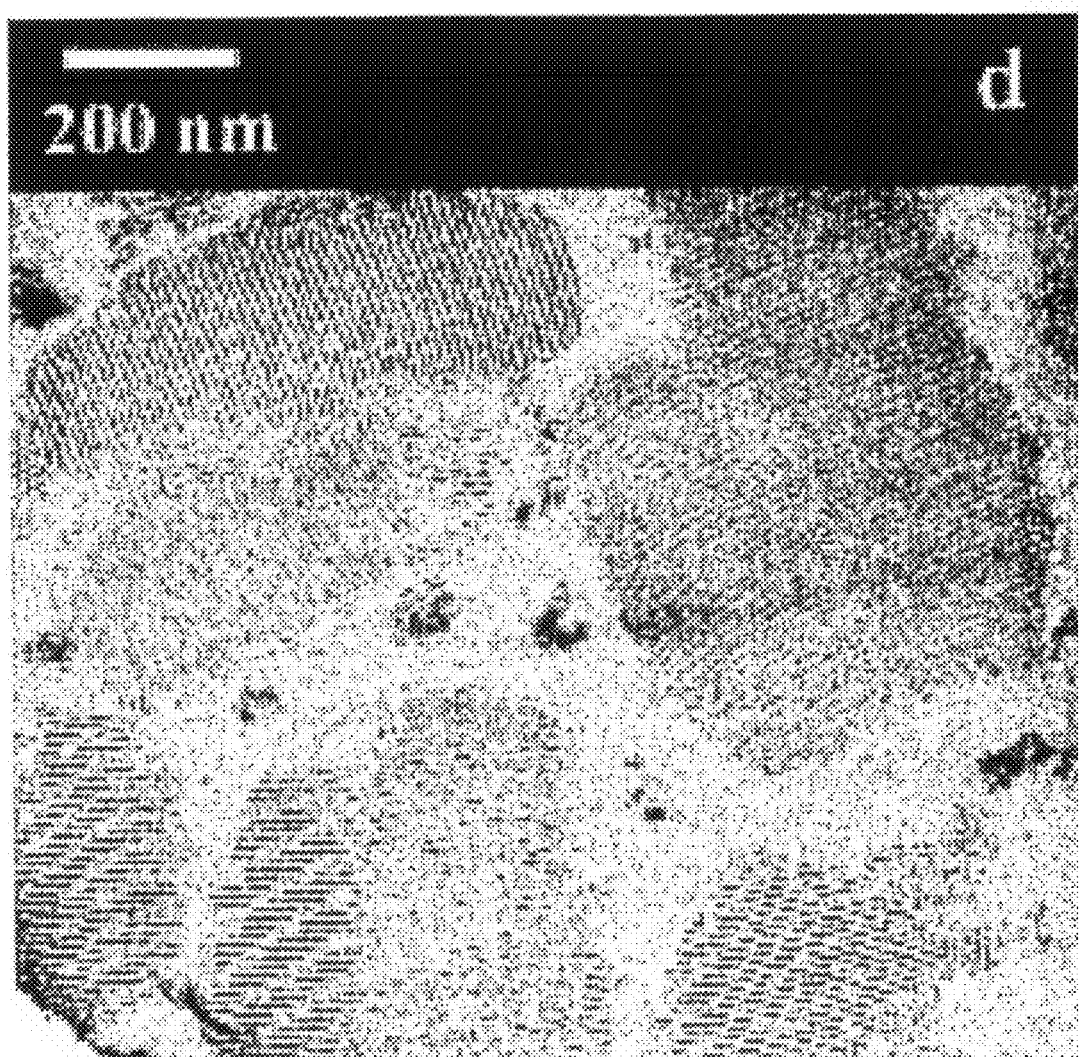
FIG. 15 is a photo showing an example of a conventional mesoporous material.
Figure 16:
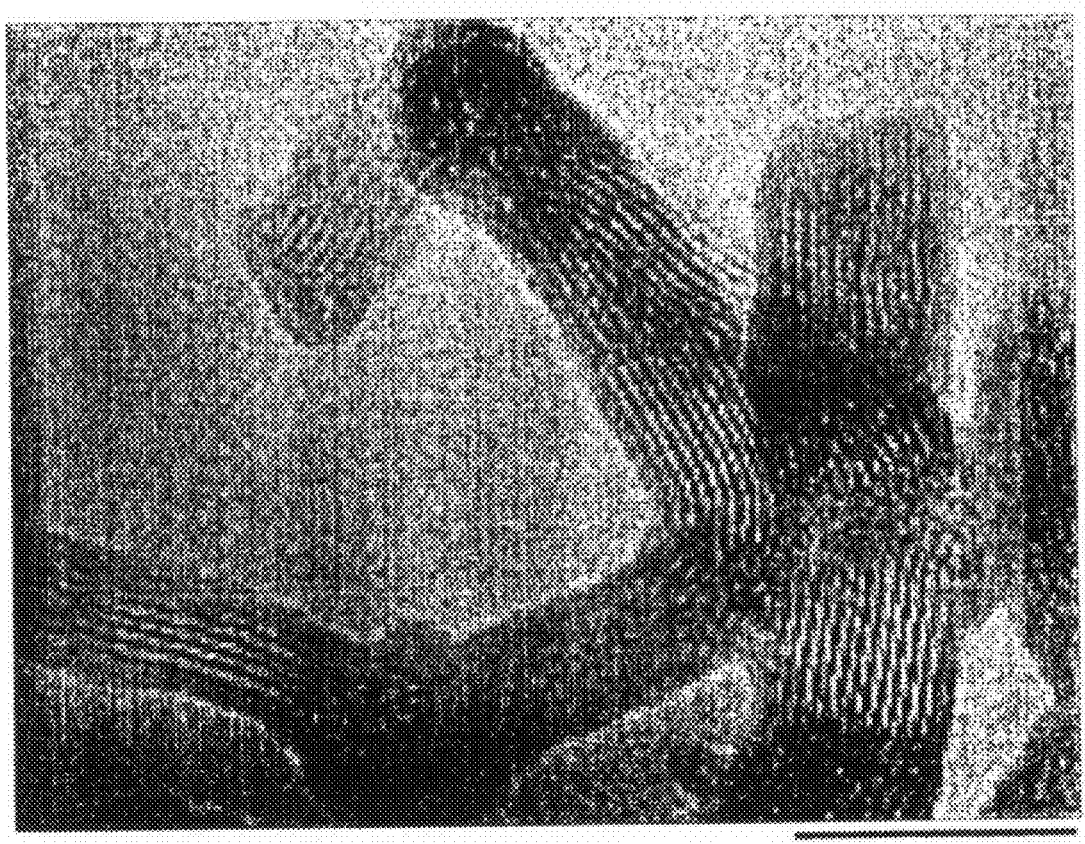
FIG. 16 is a photo showing an example of another conventional mesoporous material.

The measurement of the glucose concentration was carried out as follows. In the constant-temperature cell shown in FIG. 14, a 50 mM MOPS buffer solution was placed and maintained at a predetermined temperature. The synthesized GOD-immobilized carbon electrode was used as the working electrode 131 having enzyme-immobilized particles 130, and a platinum electrode was used as the counter electrode 132. A predetermined electric voltage was applied to the carbon electrode, and after the electric current became stationary, a sample containing glucose was added, the increase of the electric current value was measured, and a high electric current was obtained. Additionally, standard glucose solution samples were used to measure the electric current values, and consequently, the electric current value was found to linearly increase with the increase of the glucose concentration. Accordingly, there can be provided a biosensor capable of determining the glucose concentration and measuring the blood sugar level.

Example 8

This Example is a case in which the same hierarchical mesoporous silica as synthesized in Example 1 was synthesized on an electrode, further glucose oxidase (GOD) and a mediator were immobilized therein, and the glucose concentration was measured.

The hierarchical mesoporous silica is the same as in the above-mentioned working examples. Ferrocenecarboxylic acid was used as the mediator. The ferrocenecarboxylic acid was immobilized to the surface of the mesopore with a covalent bond to support GOD to the mesopore.

The immobilization of ferrocenecarboxylic acid consists of the following. A mesoporous silica-coated electrode in which mesopores had been formed by calcination was sililated with a silane coupler. 20 mM dichloromethane solution of (3-iodopropyl) trimethoxysilane (IPTMS) was prepared in a Teflon (tradename) vessel. The electrode was immersed in the solution, followed by stirring under nitrogen atmosphere at room temperature for 4 hours. The resulting electrode was washed with dichloromethane and ethanol, and dried at 80° C.

The electrode thus Iodine-propylsililated was then immersed into a mixed solution of 0.13 mM ferrocenecarboxylic acid aqueous solution and 0.17 mM N,N'-dicyclohexylcarbodiimide aqueous solution, and stirred slowly under Ar atmosphere to immobilize ferrocenecarboxylic acid on the surface of silica. The introducing of IPTMS on the surface of silica and the immobilization of ferrocenecarboxylic acid by ester bond were confirmed by FT-IR, respectively. By these steps, the immobilization of ferrocenecarboxylic acid on the surface of silica with a covalent bond was completed.

PBS with pH 7.4 was placed in a constant-temperature cell. The GOD-immobilized carbon electrode prepared above was immersed therein, followed by stirring for 5 minutes with nitrogen-bubbling, wherein an Ag—AgCl electrode as a reference electrode and a platinum wire as a counter were used. Voltages from 100 mV to 600 mV were swept over the electrode. The oxidation current became constant, and then the decreasing of the voltage was carried out, whereby a CV curve was obtained. The scan rate was set to 1 mV/s. Each time the concentration of glucose was increased, the currents were measured to determine the saturation current value. The resulting peak value of the oxidation-reduction potential was 220 mV. Thereby it was confirmed that the mediator for which ferrocenecarboxylic acid was used could be applied to a biosensor. Meanwhile, an oxidation-reduction potential in the state of allowing ferrocenecarboxylic acid floating was greater than 220 mV.

An oxidation-reduction potential when a substance in blood is oxidized/reduced by an electrode is, e.g. 500-600 mV for ascorbic acid; and 300-400 mV for hemoglobin. Accordingly, it is important for measuring correctly the peak value of current to use a mediator not overlapping these peaks of oxidation-reduction potential but having the peak in a lower potential.

That is, it is better to immobilize the mediator on the mesopore with a covalent bond than to allow it floating because the peak can be shifted to a lower potential. The reason for the shift seems to be that the mediator can be easily oxidized in the mesoporous silica governed by the negative electric field, and that the hopping of electrons is caused by the immobilization of the mediator on the surface, which makes it possible to efficiently transfer electrons to the electrode. This reason can be given for other enzymes.

As described above, according to the present invention, a new structure having mesopores can be obtained. Additionally, the mesoporous material according to the present invention is excellent in internal diffusion, and can be applied to agents for immobilizing biological materials, to the increase of the precision of column materials or to the like. The structure having mesopores according to the present invention can be applied, for example, to biosensors and the like.

Sequence Listing Free Text
<210> 1
<223> base sequence portion of probe

This application claims priority from Japanese Patent Application No. 2005-166754 filed on Jun. 7, 2005, which is hereby incorporated by reference herein.

macropore-sized voids are formed between the frameworks adjacent to one another.

3. The structure according to claim 1, wherein the mesopores are hexagonally symmetrically arranged.

4. The structure according to claim 1, wherein the mesopores have a pore size distribution in which 80% or more of the mesopores fall within a range having a width of 10 nm and a maximal value.

5. The structure according to claim 1, wherein a biological material is supported in the mesopores.

6. The structure according to claim 1, wherein 90% or more of the mesopores observable in the 500 nm×500 nm area pass through the framework in a direction perpendicular to the longitudinal direction of the framework.

7. A porous material formed into a plurality of particles, with each particle having a mesoporous silica structure with a plurality of mesopores and comprising:
    a dendritic framework having mesopores,
    wherein 90% or more of the mesopores observable in a 500 nm×500 nm area pass through the framework in a direction perpendicular to a longitudinal direction of the framework.

8. A sensor for detecting a specimen, which sensor is comprised of porous material comprising:
    a dendritic framework having mesopores,
    wherein 90% or more of the mesopores observable in a 500 nm×500 nm area pass through the framework in a direction perpendicular to a longitudinal direction of the framework; and
    an electrode, and detects an electric output signal based on a reaction between the specimen and a biological material supported in the mesopores.

9. A method for detecting a specimen, comprising the steps of:
    preparing a sensor in which a biological material is supported in mesopores of a structure having a dendritic

SEQUENCE LISTING

<160> NUMBER OF SEQ ID NOS: 1

<210> SEQ ID NO 1
<211> LENGTH: 18
<212> TYPE: DNA
<213> ORGANISM: Artificial
<220> FEATURE:
<223> OTHER INFORMATION: base sequence portion of probe

<400> SEQUENCE: 1
ataaaagtgc acaccta                                                  18

The invention claimed is:

1. A mesoporous silica structure having a plurality of mesopores, comprising:
    a dendritic framework having mesopores,
    wherein 90% or more of the mesopores observable in a 500 nm×500 nm area pass through the framework in a direction intersecting a longitudinal direction of the framework.

2. The structure according to claim 1, wherein the dendritic framework forms macropores by mutual linking of branched portions of the framework, or framework with mesopores supporting the biological material,
wherein 90% or more of the mesopores observable in a 500 nm×500 nm area pass through the framework in a direction perpendicular to a longitudinal direction of the framework,
applying a fluid that contains a specimen to the sensor; and
detecting an output signal based on a reaction between the biological material and the specimen.

* * * * *